US009427437B2

(12) United States Patent
Abboud et al.

(10) Patent No.: US 9,427,437 B2
(45) Date of Patent: *Aug. 30, 2016

(54) HYPERCHOLESTEROLEMIA AND TENDINOUS INJURIES

(71) Applicant: The Trustees of the University of Pennsylvania, Philadelphia, PA (US)

(72) Inventors: Joseph A. Abboud, Bryn Mawr, PA (US); Louis J. Soslowsky, Penn Valley, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/767,515

(22) Filed: Feb. 14, 2013

(65) Prior Publication Data
US 2013/0158058 A1 Jun. 20, 2013

Related U.S. Application Data

(63) Continuation-in-part of application No. 12/359,695, filed on Jan. 26, 2009, now Pat. No. 8,383,614.

(60) Provisional application No. 61/006,804, filed on Jan. 31, 2008.

(51) Int. Cl.
| | |
|---|---|
| *A61K 31/397* | (2006.01) |
| *A61K 31/40* | (2006.01) |
| *A61K 31/435* | (2006.01) |
| *A61K 31/404* | (2006.01) |
| *A61K 31/366* | (2006.01) |
| *A61K 31/47* | (2006.01) |
| *A61K 31/505* | (2006.01) |
| *A61K 31/351* | (2006.01) |
| *A61P 21/00* | (2006.01) |
| *C12Q 1/60* | (2006.01) |
| *A61K 31/216* | (2006.01) |
| *G01N 33/68* | (2006.01) |

(52) U.S. Cl.
CPC .......... *A61K 31/505* (2013.01); *A61K 31/216* (2013.01); *A61K 31/351* (2013.01); *A61K 31/366* (2013.01); *A61K 31/397* (2013.01); *A61K 31/40* (2013.01); *A61K 31/404* (2013.01); *A61K 31/435* (2013.01); *A61K 31/47* (2013.01); *G01N 33/6893* (2013.01); *G01N 2800/10* (2013.01)

(58) Field of Classification Search
USPC .......... 514/210.02, 423, 277, 419, 460, 311; 435/11
See application file for complete search history.

(56) References Cited

U.S. PATENT DOCUMENTS

| 6,858,618 B2 | 2/2005 | Raza et al. |
| 7,071,228 B2 * | 7/2006 | Parks ........................... 514/557 |
| 2002/0156122 A1 | 10/2002 | Mach |
| 2005/0026979 A1 | 2/2005 | Ghazzi et al. |
| 2009/0157193 A1 | 6/2009 | McKay |

OTHER PUBLICATIONS

Diomede (In Vivo Anti-Inflammatory Effect of Statins ins Mediated by Nonsterol Mevalonage Products, Arteriosclerosis, Thrombosis, and Vascular Biology, 2001, 21, pp. 1327-1332).*
Almekinders et al., "An In Vitro Investigation Into the Effects of Repetitive Motion and Nonsteroidal Antiinflammatory Medication on Human Tendon Fibroblasts" The American Journal of Sports Medicine—vol. 23, Issue 1 (Jan. 1995); 119-124.
Cohen et al., "Indomethacin and Celecoxib Impair Rotator Cuff Tendon-to-Bone Healing" The American Journal of Sports Medicine—vol. 34, No. 3 (Aug. 2006); 362-369.
Connizzo et al., "The Detrimental Effects of Systemic Ibuprofen Delivery on Tendon Healing Are Time-Dependent" (2014) Clin Orthop Relat Res., 472(8):2433-9.
Dimmen "Effects of cox inhibitors on bone and tendon healing" Acta Orthopaedica Supplementum No. 342, vol. 82 (Feb. 2011) 1-22.
Dimmen et al., "Negative effects of parecoxib and indomethacin on tendon healing: an experimental study in rats" Knee Surg Sports Traumatol Arthrosc (2009) 17:835-839.
Dolkart et al., "Statins Enhance Rotator Cuff Healing by Stimulating the COX2/PGE2/EP4 Pathway" (2014) The American Journal of Sports Medicine, vol. 42, No. 12; 2869-2876.
Ferry et al., "The Effects of Common Anti-Inflammatory Drugs on the Healing Rat Patellar Tendon" The American Journal of Sports Medicine—vol. 35, No. 8 (Apr. 2007) 1326-1333.
Forslund et al., "Indomethacin and celecoxib improve tendon healing in rats" Acta Orthop Scan 2003; vol. 74, No. 4 465-469.
Madsen et al., "Negative effects of parecoxib and indomethacin on tendon healing: an experimental study in rats" Knee Surg Sports Traumatol Arthrosc (Mar. 2009) vol. 17:835-839.
Tsai et al., "Effects of Celecoxib on Migration, Proliferation and Collagen Expression of Tendon Cells" Connective Tissue Research, (2007) vol. 48; 46-51.

(Continued)

*Primary Examiner* — Kathrien Cruz
(74) *Attorney, Agent, or Firm* — Mark S. Cohen; Pearl Cohen Zedek Latzer Baratz LLP

(57) ABSTRACT

This invention provides compositions and methods of inhibiting, suppressing, or treating a tendinous or musculoskeletal soft tissue injury. The invention further provides a method of ameliorating symptoms associated with a tendinous or musculoskeletal soft tissue injury. Additionally, the invention provides methods for evaluating the risk of developing a tendinous or musculoskeletal soft tissue injury.

23 Claims, 12 Drawing Sheets

(56) References Cited

OTHER PUBLICATIONS

Tsai et al., "Ibuprofen Inhibition of Tendon Cell Migration and Down-Regulation of Paxillin Expression" Orthopaedic Research Society. Published by Wiley Periodicals, Inc. (2006) 551-558.
Virchenko et al., "Parecoxib Impairs Early Tendon Repair but Improves Later Remodeling" The American Journal of Sports Medicine—vol. 32, No. 7 (2004); 1743-1747.
Langer, "New methods of drug delivery", Science 249:1527-1533 (1990).
Treat et al., "Liposome incapsulated doxorubicin preliminary results of Phase I and Phase II trials", Liposomes in the Therapy of Infectious Disease and Cancer, pp. 353-365 (1989).
Lopez-Berestein, "Treatment of systemic fungal infections with liposomal-amphotericin B", Liposomes in the Therapy of Infectious Diseases and Cancer, pp. 317-327.
Sefton, "Implatnable pumps", CRC Crit. Ref. Biomed. Eng. 14:201 (1987).
Buchwald et al., "Long-term, continuous intravenous heparin administration by an implantable infusion pump in ambulatory patients with recurrent venous thrombosis" Surgery 88:507 (1980).
Saudek et al., "A preliminary trial of the programmable implantable medication system for insulin delivery", N. Engl. J. Med. 321:574 (1989).
Goodson, "Dental applications" Medical Applications of Controlled Release, supra, vol. 2, pp. 115-138 (1984).

\* cited by examiner

A

B

HYPERCHOLESTEROLEMIA AND TENDINOUS INJURIES

CROSS REFERENCE TO RELATED APPLICATIONS

This application is a continuation-in-part of U.S. patent application Ser. No. 12/359,695, filed Jan. 26, 2009, claims priority to U.S. Provisional Patent Application No. 61/006,804, filed Jan. 31, 2008, each of which is hereby incorporated by reference in its entirety.

FIELD OF INVENTION

The invention relates to compositions and methods for treating, reducing the incidence of, and detecting a tendon injury. Specifically, the invention relates to administering a cholesterol lowering agent to treat or reduce the incidence of a tendon injury.

BACKGROUND OF THE INVENTION

Musculoskeletal soft tissue injuries from athletic activities are common in the rotator cuff tendons, lateral epicondyle of the elbow, the patella tendon, and the achilles tendon. Despite the fact that the achilles tendon is the largest and strongest tendon in the human body, it is frequently injured in the athletic setting.

Achilles tendon injuries range from inflammation of the paratendinous tissue, to structural degeneration of the tendon (tendinosis), and finally, to tendon rupture. The most common clinical presentation of achilles tendon injuries is tendinopathy. It is characterized by a combination of pain and swelling in the achilles tendon accompanied by impaired ability to participate in strenuous activity. Many achilles tendon ruptures occur without precipitating signs and symptoms and it is widely accepted that surgical repair should be performed in physically active patients. To better prevent and treat injuries to the Achilles tendon, it is necessary to understand the etiology and pathogenesis of the disease process.

Intrinsic, extrinsic, and overuse activity are well-known factors responsible for tendinous injuries in general. Previous studies on the achilles tendon were often from a surgical reconstructive or clinical retrospective standpoint. While important, these studies were not designed to determine the roles of disease etiology and pathogenesis. Accordingly, a need exists to determine the roles of disease etiology and pathogenesis, and thereby develop improved compositions and methods for treating tendinous injuries.

SUMMARY OF THE INVENTION

In one aspect, methods are provided herein for treating a tendinous or musculoskeletal soft tissue injury, in a subject (e.g., a subject with hypercholesterolemia), the methods comprising: administering (e.g., systemically) to said subject a therapeutically effective amount of a cholesterol lowering agent (e.g., a statin), wherein said soft tissue injury is a tendon injury.

In another aspect, methods are provided herein for reducing the incidence of a tendinous or musculoskeletal soft tissue injury, in a subject (e.g., a subject with hypercholesterolemia) at risk of developing a tendon injury, the methods comprising: administering (e.g., systemically) to said subject a therapeutically effective amount of a cholesterol lowering agent (e.g., a statin), wherein said soft tissue injury is a tendon injury.

In a further aspect, methods are provided herein for inhibiting or suppressing a tendinous or musculoskeletal soft tissue injury, in a subject (e.g., a subject with hypercholesterolemia), the methods comprising: administering (e.g., systemically) to said subject a therapeutically effective amount of a cholesterol lowering agent (e.g., a statin), wherein said soft tissue injury is a tendon injury.

In an additional aspect, methods are provided herein for ameliorating symptoms associated with a tendinous or musculoskeletal soft tissue injury, in a subject (e.g., a subject with hypercholesterolemia), the methods comprising: administering (e.g., systemically) to said subject a therapeutically effective amount of a cholesterol lowering agent (e.g., a statin), wherein said soft tissue injury is a tendon injury.

In yet another aspect, methods are provided herein for accelerating the healing of a tendinous or musculoskeletal soft tissue injury, in a subject (e.g., a subject with hypercholesterolemia), the methods comprising: administering (e.g., systemically) to said subject a therapeutically effective amount of a cholesterol lowering agent (e.g., a statin), wherein said soft tissue injury is a tendon injury.

In yet an additional aspect, methods are provided for preserving a biomechanical property of a tendon in a subject (e.g., a subject with hypercholesterolemia), the methods comprising: administering (e.g., systemically) to said subject a therapeutically effective amount of a cholesterol lowering agent (e.g., a statin), wherein said soft tissue injury is a tendon injury.

In yet a further aspect, methods are provided for evaluating the risk of developing a tendinous or musculoskeletal soft tissue injury, in a subject, comprising the steps of: obtaining a biological sample from a subject; analyzing the concentration of TC, HDL-C, LDL-C, TG or their combination; and comparing the concentration to a standard, whereby if the concentration of TC, HDL-C, LDL-C, TG or their combination is different than the concentration of said standard, the subject is in high risk of developing a tendinous or musculoskeletal soft tissue injury.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The invention will be better understood from a reading of the following detailed description taken in conjunction with the drawings in which like reference designators are used to designate like elements, and in which.

Normalized maximum stress in injured tendons recovered significantly closer to baseline (value of 1.0) for CTL mice.

Figure 6:
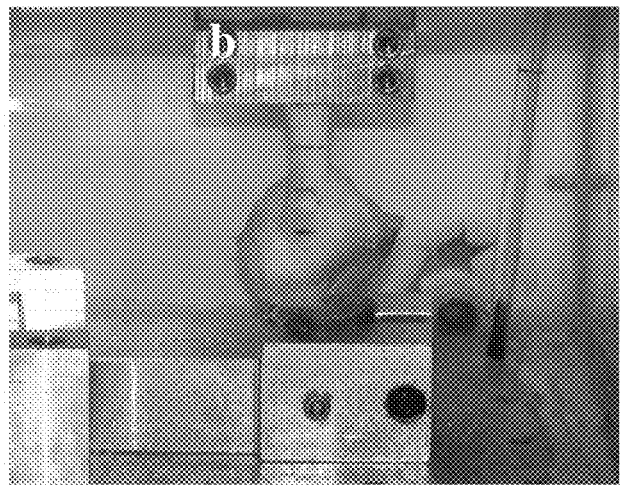
Figure 6:
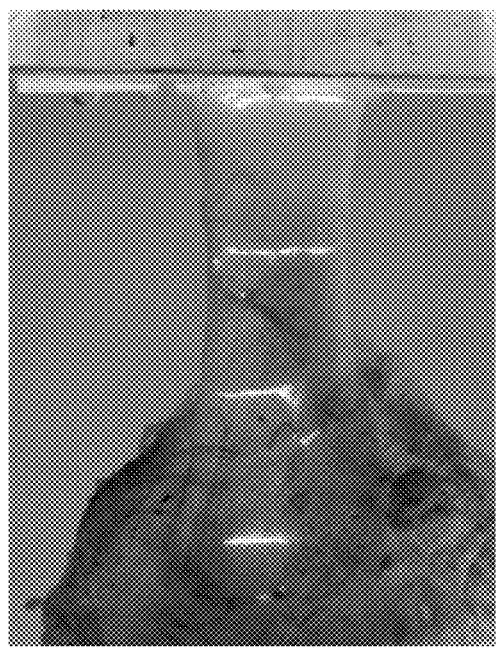

FIG. 6 shows (a) Pig biceps tendon placed in test fixture, submerged in PBS bath at body temperature; and (b) shown during tensile testing.

Figure 7:
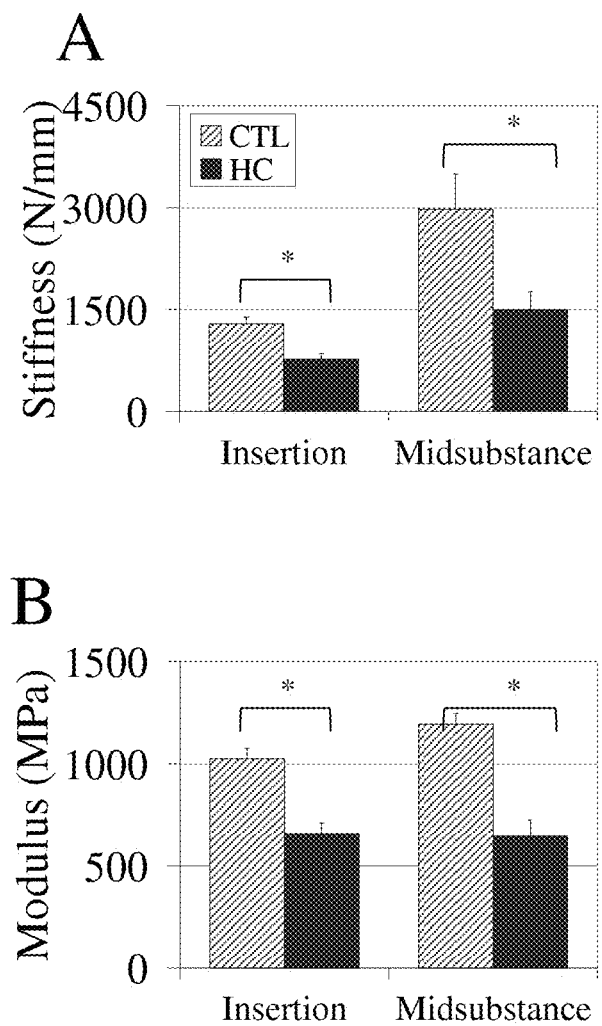

FIG. 7 shows that stiffness and modulus were significantly reduced (*) in the high cholesterol (HC) tendons compared to control (CTL) both at the insertion site and in the tendon midsubstance.

Figure 8:
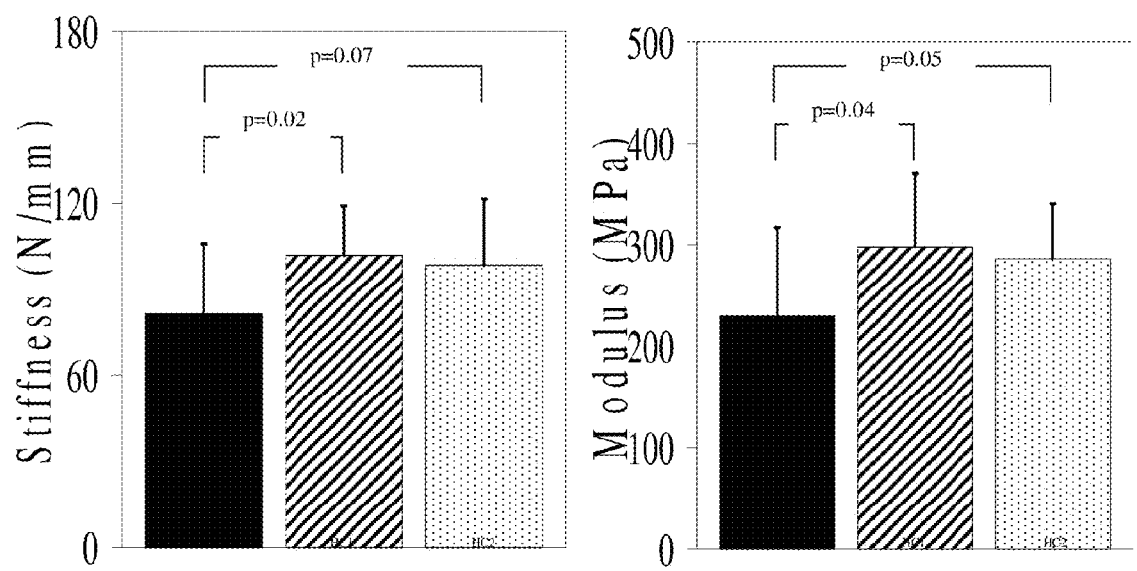

FIG. 8 shows that stiffness and modulus of both HC1 and HC2 were significantly increased compared to CTL.

Figure 9:
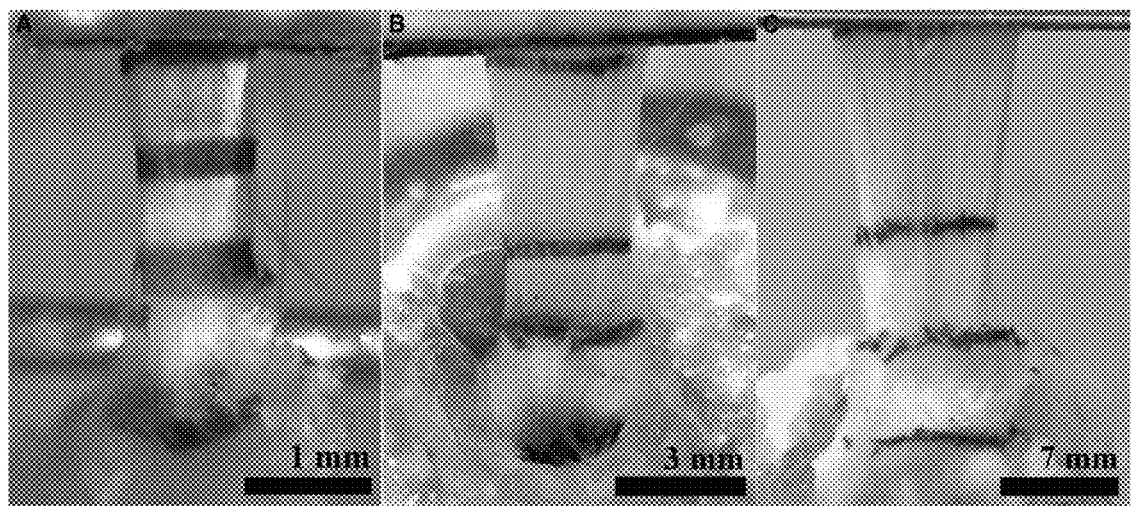

FIG. 9 shows supraspinatus tendons with stain lines applied from mouse (A), rat (B), and monkey (C).

Figure 10:
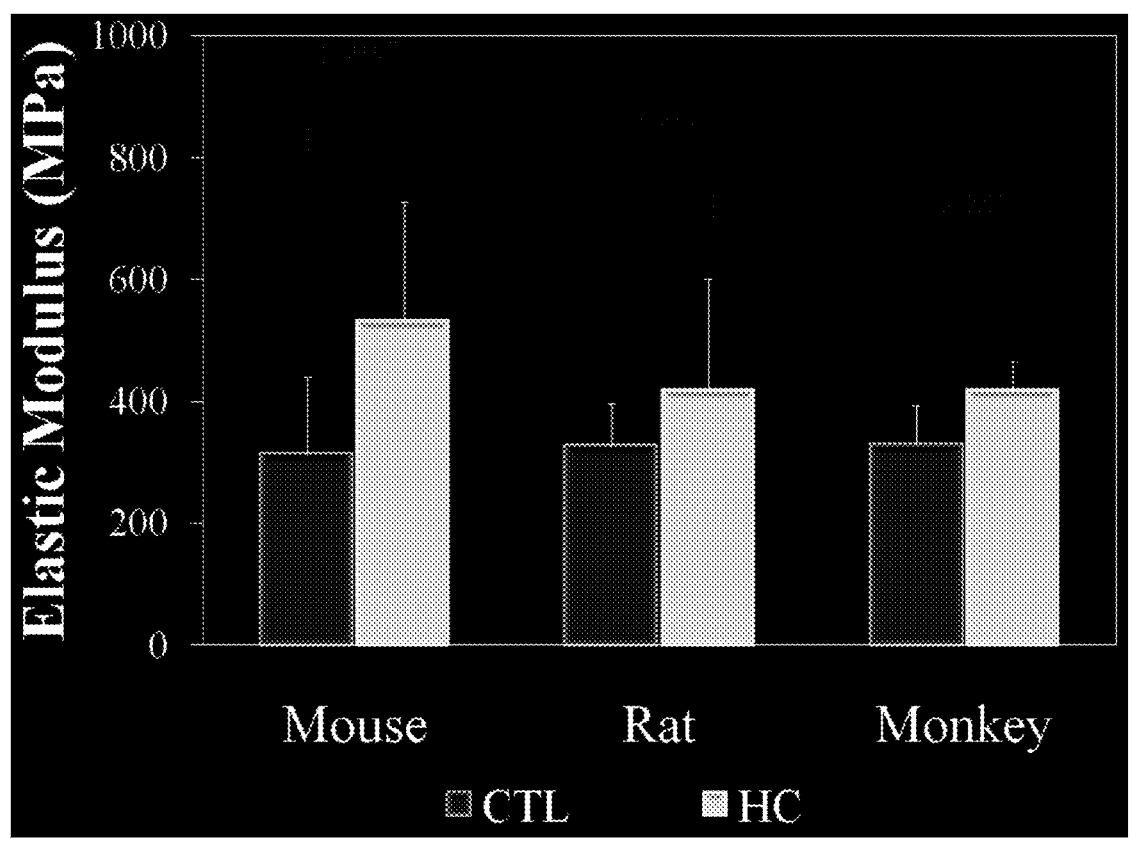

FIG. 10 shows that moduli were increased in HC tendons compared to CTL across species.

Figure 11:
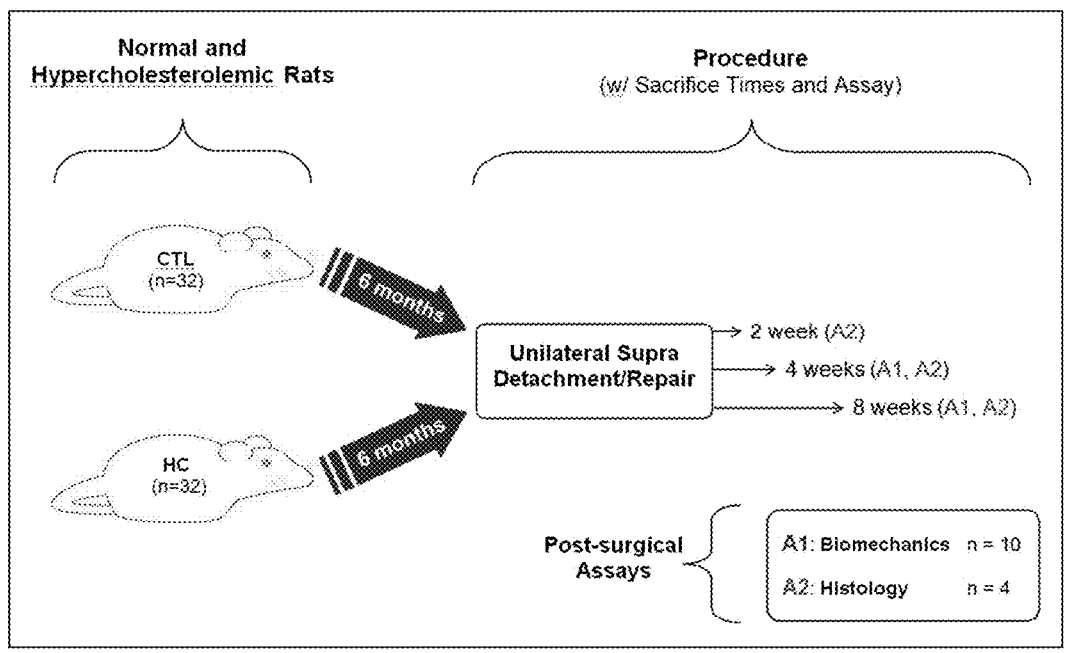

FIG. 11 shows the study design of Example 8.

Figure 12:
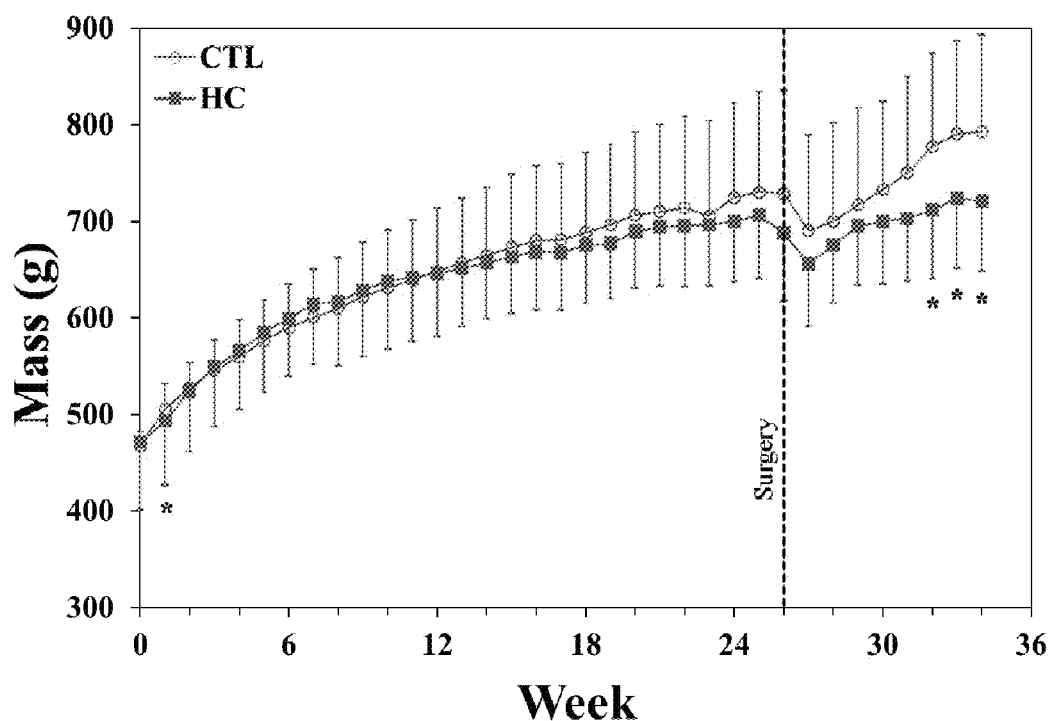

FIG. 12 shows masses of rats over the course of the study. Significant differences (*) were noted at the first week on the HC diet and in the final 3 weeks for the 8-week animals.

DETAILED DESCRIPTION OF THE INVENTION

The invention relates to compositions and methods for treating, reducing the incidence of, and detecting a tendon injury. In particular, the invention relates to administering a cholesterol lowering agent to treat or reduce the incidence of a tendon injury.

In one embodiment, the invention provides a method of treating a subject afflicted with a tendinous or musculoskeletal soft tissue injury. The method comprises administering to a subject a therapeutically effective amount of a cholesterol lowering agent.

As used herein, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disorder after a remission. For example, for a subject at risk of developing a tendon injury who previously had that tendon injury, reducing the incidence of said tendon injury comprises reducing the risk of recurrence of the tendon injury. Subjects at particular risk of a tendon injury, whether an occurrence or a recurrence of a tendon injury, include manual laborers, diabetics, high performance and recreational athletes, smokers, diabetics, and overweight or obese subjects.

As used herein, the term "administering" refers to bringing a subject in contact with an agent of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject. The term "subject," as used herein, includes any human or non-human animal. The term "non-human animal" includes all vertebrates, e.g., mammals and non-mammals.

In certain embodiments, the cholesterol lowering agent is a HMG-CoA reductase inhibitor or "statin." In other embodiments, the cholesterol lowering agent increases the clearance of low-density lipoprotein (LDL) from the bloodstream.

Statins include, but are not limited to, atorvastatin, cerivastatin, lovastatin, mevastatin, fluvastatin, pitavastatin, pravastatin, rosuvastatin, simvastatin or any combination thereof. In another embodiment, the cholesterol lowering agent is ezetimibe. In another embodiment, the cholesterol lowering agent is a composition comprising simvastatin and ezetimibe. In another embodiment, the cholesterol lowering agent is a composition comprising lovastatin and niacin. In another embodiment, the cholesterol lowering agent is a composition comprising simvastatin and niacin. In another embodiment, the cholesterol lowering agent is a composition comprising atorvastatin and amlodipine. In another embodiment, the cholesterol lowering agent is a composition comprising niacin.

Proprotein convertase subtilisin/kexin type 9 (PCSK9) helps regulate cholesterol levels in the blood stream and its inhibition has been shown to lower cholesterol levels. PCSK9 inhibitors can be used as a cholesterol lowering agents. Known PCSK9 inhibitors include monoclonal antibodies to PCSK9, peptide mimics to PCSK9, antisense molecules to PCSK9 mRNA and siRNA targeting PCSK9.

Among other things, cholesterol comprises low-density lipoprotein (LDL) and high-density lipoprotein (HDL).

As used herein, hypercholesterolemia encompasses a blood cholesterol concentration greater than 200 mg/dL, more preferably greater that 220 mg/dL and most preferably 240 mg/dL. In certain embodiments, the cholesterol lowering agent lowers a subject's blood total cholesterol concentration below about 240 mg/dL. In certain embodiments, the cholesterol lowering agent lowers a subject's blood total cholesterol concentration below about 220 mg/dL. In certain embodiments, the cholesterol lowering agent lowers a subject's blood total cholesterol concentration below about 200 mg/dL.

In certain embodiments, the cholesterol lowering agent lowers a subject's blood total Low-density lipoprotein-C (LDL) to below about 130 mg/DL. In certain embodiments, the cholesterol lowering agent lowers a subject's blood total LDL-C to below about 120 mg/DL. In certain embodiments, the cholesterol lowering agent lowers a subject's blood total LDL-C to below about 110 mg/DL. In certain embodiments, the cholesterol lowering agent lowers a subject's blood total LDL-C to below about 100 mg/DL.

In certain embodiments, the cholesterol lowering agent raises a subject's blood total High-density lipoprotein-C (HDL) to above about 40 mg/DL. In certain embodiments, the cholesterol lowering agent raises a subject's blood total HDL-C to above about 45 mg/DL. In certain embodiments, the cholesterol lowering agent raises a subject's blood total HDL-C to above about 50 mg/DL. In certain embodiments, the cholesterol lowering agent raises a subject's blood total HDL-C to above about 55 mg/DL. In certain embodiments, the cholesterol lowering agent raises a subject's blood total HDL-C to above about 60 mg/DL.

In certain embodiments, the cholesterol lowering agent lowers a subject's blood total triglycerides (TG) to below about 150 mg/DL. In certain embodiments, the cholesterol lowering agent lowers a subject's blood total TG to below about 140 mg/DL. In certain embodiments, the cholesterol lowering agent lowers a subject's blood total TG to below about 130 mg/DL. In certain embodiments, the cholesterol lowering agent lowers a subject's blood total TG to below about 120 mg/DL.

In certain embodiments, the cholesterol lowering agent lowers a subject blood total cholesterol concentration below about 240 mg/dL, LDL-C to below about 130 mg/DL, TG to below about 150 mg/DL, and raises HDL-C to above about 40 mg/DL. In certain embodiments, the cholesterol lowering agent lowers a subject blood total cholesterol concentration below about 240 mg/dL, LDL-C to below about 130 mg/DL, TG to below about 150 mg/DL, and raises HDL-C to above about 40 mg/DL.

In certain embodiments, the tendon injuries comprise chronic degenerative changes.

Tendon injuries, include but are not limited to, a rotator cuff injury, a knee tendon injury, a wrist tendon injury, an elbow tendon injury, tennis elbow (lateral epicondylitis), golfer's elbow (medial epicondylitis), a flexor tendon injury, an extensor tendon injury, an achilles tendon injury, a patellar tendon injury, a peroneal tendon injury, a biceps tendon injury, or an overuse tendon injury. In some cases, the subject may have any combination of the foregoing tendon injuries, e.g., a rotator cuff injury and an elbow-tendon injury. In some instance, the subject with the tendon injury is a child.

As used herein, the term "tendon injury" includes a tendinopathy, a torn tendon, a painful tendon, a series of microtears in the connective tissue or around the tendon, tendinitis and tendinosis.

In certain embodiments, the musculoskeletal soft tissue injury and/or tendon injury is associated with disorders such as osteoarthritis and rheumatoid arthritis. In certain embodiments, the cholesterol lowering agent is used to treat, prevent, or reduce the symptoms associated with a musculoskeletal soft tissue injury and/or a tendon injury, wherein the musculoskeletal soft tissue injury and/or tendon injury is associated with disorders such as osteoarthritis and rheumatoid arthritis. In certain embodiments, a statin is used to treat, prevent, or reduce the symptoms associated with a musculoskeletal soft tissue injury and/or a tendon injury, wherein the musculoskeletal soft tissue injury and/or tendon injury is associated with disorders such as osteoarthritis and rheumatoid arthritis.

In certain embodiments, the methods provided herein further comprise treating inflammation associated with a tendinous injury or a musculoskeletal soft tissue injury. In certain embodiments, the methods provided herein further comprise treating edema associated with a tendinous injury or a musculoskeletal soft tissue injury.

A tendon injury usually can be diagnosed with a review of medical history and recent activities and a physical examination. In general, treatment progress is monitored by periodic assessment of tendon/ligament-like tissue formation, or tendon or ligament growth and/or repair. The progress can be monitored by methods known in the art, for example, X-rays, arthroscopy, surgery, histomorphometric determinations, ultrasound, magnetic resonance image (MRI), tetracycline labeling and CT scanning.

In certain embodiments, valid tests are provided based on the interaction of elevated cholesterol levels and tendon pathology. In certain embodiments, valid tests are provided based on the interaction of elevated cholesterol levels and tendon healing. In certain embodiments, the tendon injuries comprise chronic degenerative changes.

Applicants have determined that hypercholesterolemia affects the biomechanical, histologic (organizational) and immunohistochemical properties of tendons. Without wishing to be bound by theory, increased levels of cholesterol lead to reduced collagen organization within the tendon and to inferior biomechanical properties.

Applicants have determined that hypercholesterolemia affects the mechanical and organizational properties of tendons. In some cases, the present invention provides that hypercholesterolemia affects the mechanical and organizational properties of tendons after injury. In some cases, hypercholesterolemia causes hyper sensitivity to tendon injury. In some cases, a subject afflicted with hypercholesterolemia has increased probability to develop a tendon injury. In some cases, tendon injury can serve as a preliminary marker to hypercholesterolemia. In some cases, a subject afflicted with tendon injury has increased probability to develop hypercholesterolemia.

Altering cholesterol levels affect the mechanical properties of repairing tendon. More specifically, elevated cholesterol levels affect the mechanical properties of repairing tendon.

In some cases, tendons of a hypercholesterolemic subject, the material properties (e.g., stress, modulus) are inferior to controls and remain so over time. In some cases, the structural mechanical properties (e.g., load, stiffness) of tendons of a hypercholesterolemic subject approach normal over time due to an increase in cross-sectional area associated with increased fibrosis.

In another embodiment, the present invention provides that hypercholesterolemia affects the organizational properties of a musculoskeletal soft tissue. In another embodiment, the present invention provides that hypercholesterolemia affects the mechanical and organizational properties of a musculoskeletal soft tissue after injury. In another embodiment, the present invention provides that hypercholesterolemia causes hyper sensitivity to a musculoskeletal soft tissue injury. In another embodiment, the present invention provides that a subject afflicted with hypercholesterolemia has increased probability to develop a musculoskeletal soft tissue injury. In another embodiment, the present invention provides that a musculoskeletal soft tissue injury can serve as a preliminary marker to hypercholesterolemia. In another embodiment, the present invention provides that a subject afflicted with a musculoskeletal soft tissue injury has increased probability to develop hypercholesterolemia.

In another embodiment, the present invention provides that alterations in cholesterol levels affect the mechanical properties of repairing a musculoskeletal soft tissue injury. In another embodiment, the present invention provides that elevated cholesterol levels affect the mechanical properties of repairing musculoskeletal soft tissue injury. In another embodiment, the present invention provides that elevated cholesterol levels inhibit the mechanical properties of repairing a musculoskeletal soft tissue injury.

In another embodiment, the present invention provides that in musculoskeletal soft tissue injury of hypercholesterolemic subject, the material properties (e.g., stress, modulus) are inferior to controls and remain so over time. In another embodiment, the present invention provides that in musculoskeletal soft tissue injury of hypercholesterolemic subject, the structural mechanical properties (e.g., load, stiffness) approach normal over time due to an increase in cross-sectional area associated with increased fibrosis.

In another embodiment, the present invention provides that cholesterol lowering drugs reduce pain associated with musculoskeletal injuries. In another embodiment, the present invention provides that cholesterol lowering drugs promote healing of musculoskeletal soft tissue injuries. In another embodiment, the present invention provides that cholesterol lowering drugs would improve the ability to both treat and prevent musculoskeletal injuries and/or tendon injuries.

In another embodiment, the present invention provides that cholesterol lowering drugs improve revascularization problems associated with tendon ruptures. In another embodiment, the present invention provides that cholesterol lowering drugs inhibit degenerative changes associated with tendon ruptures.

In yet an additional aspect, methods are provided for preserving a biomechanical property of a tendon in a subject (e.g., a subject with hypercholesterolemia), the methods comprising: administering (e.g., systemically) to said subject a therapeutically effective amount of a cholesterol lowering agent (e.g., a statin), wherein said soft tissue injury is a tendon injury.

In another embodiment, the present invention provides that evaluation of mechanical parameters at various stages of tendon injury show that a low level of injury is characterized by changes in the tendon's elongation without compromise in the stiffness. In another embodiment, the present invention provides that the varying responses of elongation, stiffness and hysteresis at increasing levels of injury reflect the mechanistic changes that underlie the process by which the tendon degenerates from subrupture loads.

In another embodiment, the present invention provides a method of evaluating the risk of a subject developing a tendinous or a musculoskeletal soft tissue injury in a subject, comprising the steps of: obtaining a biological sample from a subject; analyzing the concentration of TC, HDL-C, LDL-C, TG or their combination; and comparing the concentration to a standard, whereby if the concentration of TC, HDL-C, LDL-C, TG or their combination is different than a pre-determined threshold, the subject is in high risk of developing a tendinous or a musculoskeletal soft tissue injury. In another embodiment, the present invention provides a method of evaluating the risk of a subject developing a tendinous or a musculoskeletal soft tissue injury in a subject, comprising the steps of: obtaining a biological sample from a subject; analyzing the concentration of TC, HDL-C, LDL-C, TG or their combination; and comparing the concentration to a standard, whereby if the concentration of TC, HDL-C, LDL-C, TG or their combination is higher than a pre-determined threshold, the subject is in high risk of developing a tendinous or a musculoskeletal soft tissue injury. In another embodiment, the present invention provides that the standard is taken from a subject or a pool of subject with a low risk of developing a tendinous or a musculoskeletal soft tissue injury. In another embodiment, the present invention provides that the standard is taken from a subject or a pool of subject with a high risk of developing a tendinous or a musculoskeletal soft tissue injury. In another embodiment, the present invention provides that the biological sample is blood, plasma, sera, saliva urine, tendon tissue, or any combination thereof.

In another embodiment, the present invention provides a kit for diagnosing the risk of a subject developing a tendinous or a musculoskeletal soft tissue injury in a subject, comprising reagents, packaging and instructions for analyzing the concentration of TC, HDL-C, LDL-C, TG or their combination in a biological sample of the subject. In another embodiment, the present invention provides that the instruction comprise a pre-determined threshold for the concentration of said TC, HDL-C, LDL-C, TG in the biological sample.

In another embodiment, the invention provides a method of improving a response to treatment of a tendinous or musculoskeletal soft tissue injury, in a subject, comprising administering to said subject a first agent and a second agent, wherein said first agent is a therapeutic molecule for treating said tendinous or musculoskeletal soft tissue injury and said second agent is a cholesterol lowering agent. In certain embodiments, the first and second agents are co-administered. In certain embodiments, the first and second agents are administered separately at different times.

Examples of a therapeutic molecule for treating tendinous injury include, but are not limited to, non-steroidal anti-inflammatory drugs (NSAIDs) and cortisone. Examples of NSAIDs include, but are not limited to, salicylate such as acetylsalicylic acid, amoxiprin, benorylate, choline magnesium salicylate, diflunisal, ethenzamide, faislamine, methyl salicylate, magnesium salicylate, salicyl salicylate, and salicylamide; arylalkanoic acid such as diclofenac, aceclofenac, alclofenac, bromfenac, etodolac, indomethacin, nabumetone, oxametacin, proglumetacin, sulindac, and tolmetin; 2-Arylpropionic acid (profens) such as ibuprofen, alminoprofen, benoxaprofen, carprofen, dexibuprofen, dexketoprofen, fenbufen, fenoprofen, flunoxaprofen, flurbiprofen, ibuproxam, indoprofen, ketoprofen, ketorolac, loxoprofen, naproxen, oxaprozin, pirprofen, suprofen, and tiaprofenic acid, N-Arylanthranilic acid (fenamic acid) such as mefenamic acid, flufenamic acid, meclofenamic acid, and tolfenamic acid; pyrazolidine derivative such as phenylbutazone, ampyrone, azapropazone, clofezone, kebuzone, metamizole, mofebutazone, oxyphenbutazone, phenazone, and sulfinpyrazone; oxicam such as piroxicam, droxicam, lornoxicam, meloxicam, and tenoxicam; COX-2 inhibitor such as celecoxib, etoricoxib, lumiracoxib, parecoxib, rofecoxib, and valdecoxib; and sulphonanilide such as nimesulide; licofelone and an omega-3 fatty acid.

In another embodiment, the invention provides a pharmaceutical composition of treating a tendinous or musculoskeletal soft tissue injury, in a subject, comprising a therapeutically effective amount of a cholesterol lowering agent.

In one embodiment, the present invention relates to the use of a cholesterol lowering compound and/or its analog, derivative, isomer, metabolite, pharmaceutically acceptable salt, pharmaceutical product, hydrate, N-oxide, or combinations thereof for treating, preventing, suppressing, inhibiting or reducing the incidence of a tendinous or musculoskeletal soft tissue injury. Thus, in certain embodiments, the methods provided herein comprise administering an analog of the cholesterol lowering compound. In certain embodiments, the methods provided herein comprise administering a derivative of the cholesterol lowering compound. In certain embodiments, the methods provided herein comprise administering an isomer of the cholesterol lowering compound. In certain embodiments, the methods provided herein comprise administering a metabolite of the cholesterol lowering compound. In certain embodiments, the methods provided herein comprise administering a pharmaceutically acceptable salt of the cholesterol lowering compound. In certain embodiments, the methods provided herein comprise administering a pharmaceutical product of the cholesterol lowering compound. In certain embodiments, the methods provided herein comprise administering a hydrate of the cholesterol lowering compound. In certain embodiments, the methods provided herein comprise administering an N-oxide of the cholesterol lowering compound. In certain embodiments, the methods provided herein comprise administering any of a combination of an analog, derivative, isomer, metabolite, pharmaceutically acceptable salt, pharmaceutical product, hydrate or N-oxide of the cholesterol lowering compound.

Compositions described herein may include a "therapeutically effective amount" of an agent. A "therapeutically effective amount" refers to an amount effective, at dosages and for periods of time necessary, to achieve the desired therapeutic result. A therapeutically effective amount may vary according to factors such as the disease state, age, sex, and weight of the individual, and the ability of the agent to elicit a desired response in the individual. A therapeutically effective amount is also one in which any toxic or detrimental effects of the agent are outweighed by the therapeutically beneficial effects. As used herein, "pharmaceutical composition" means a "therapeutically effective amount" of the active ingredient(s), e.g., the cholesterol lowering agent (e.g., a statin), together with at least one pharmaceutically acceptable carrier or diluent.

The pharmaceutical compositions of the invention can be administered to a subject by any method known to a person skilled in the art, such as parenterally, paracancerally, trans-mucosally, trans-dermally, intramuscularly, intravenously, intra-dermally, subcutaneously, intra-peritonealy, intra-ventricularly, intra-cranially, intra-vaginally or intra-tumorally.

In certain embodiments, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In certain embodiments, the cholesterol lowering compounds are formulated in a capsule. In accordance with this embodiment, the compositions may comprise inert carrier, diluent, or a hard gelating capsule.

Further, in another embodiment, the pharmaceutical compositions are administered by intravenous, intra-arterial, or intramuscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intramuscular administration.

Further, in another embodiment, the pharmaceutical compositions are administered topically to body surfaces and are thus formulated in a form suitable for topical administration. Suitable topical formulations include gels, ointments, creams, lotions, drops and the like. For topical administration, the cholesterol lowering agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of a cholesterol lowering agent over a period of time.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof. Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled-release compositions, i.e. compositions in which the apoptosis-modifying compound is released over a period of time after administration. Controlled- or sustained-release compositions include formulation in lipophilic depots (e.g. fatty acids, waxes, oils). In another embodiment, the composition is an immediate-release composition, i.e. a composition in which all of the apoptosis-modifying compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled-release systems are discussed in the review by Langer (Science 249:1527-1533 (1990)).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds. Such modifications may also increase the compounds solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the cholesterol lowering agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the cholesterol lowering agents or their physiologically tolerated derivatives such as salts, esters, N-oxides, and the like are converted into a solution, suspension, or emulsion, if desired with the substances customary and suitable for this purpose, for example, solubilizers or other substances.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, the compositions of the invention are administered in conjunction with other therapeutic agents. In another embodiment, the compositions of the invention are administered in conjunction with surgery or other therapy, to a patient who has a tendinous injury or a risk of developing tendinous injury.

In one example, the compositions of the present invention are administered to a patient in conjunction with a non-steroidal anti-inflammatory drug (NSAID). In another example, the compositions of the present invention are administered to a patient in conjunction with a cortisone drug. The compositions of the present invention may be administered in combination with one or more other prophylactic or therapeutic agents, including but not limited to cytotoxic agents, chemotherapeutic agents, cytokines, growth inhibitory agents, antihormonal agents, kinase inhibitors, cardioprotectants, immunostimulatory agents, immunosuppressive agents, agents that promote proliferation of tendinous or musculoskeletal soft tissue cells, protein tyrosine kinase (PTK) inhibitors, antibodies, or other therapeutic agents. In a particular embodiment, the methods of the present invention comprise administering a statin in combination with one or more therapeutic agents.

Dosage regimens may be adjusted to provide the optimum desired response. For example, a single dose may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of an agent calculated to produce the desired therapeutic effect in association with the required pharmaceutical carrier. For any particular patient or subject, specific dosage regimens may be adjusted over time according to the individual need and the professional judgment of the person administering or supervising the administration of the compositions.

EXAMPLES

Experimental Details

Description of Overall Experiments

The purpose of the first experiment is to determine the biomechanical, histologic (organizational) and Immunohistochemical properties of the uninjured patellar tendon in an environment of hypercholesterolemia. Mice are sacrificed at 13 weeks of age. Subsequently immunohistochemistry, histology, and biomechanics aspects are assessed.

The purpose of the second experiment is to determine the biomechanical, histologic (organizational) and immunohistochemical properties of the healing tendon in an environment of hypercholesterolemia. From this group, four mice are sacrificed 5 days post-surgery for the immunohistochemistry study, while four mice are sacrificed at 3 weeks post-surgery (13 weeks of age) for the histologic study and the remaining ten mice are sacrificed at 3 weeks post-surgery for the biomechanical study. For the experimental group, 18 mice are used.

Five days post-injury has been chosen for the immunohistochemistry assay based on the fact that cytokine expression occurs during the first (inflammatory) phase of tendon healing. It has also been a time point used for immunohistochemistry in previous studies utilizing this patellar tendon injury model. Three weeks post-injury has been chosen for histologic (organizational) and biomechanical study since by three weeks post-injury, a balance between collagen synthesis and breakdown has been reached and remodeling has begun.

Specimen Size Justification

Based on previous mouse patellar tendon biomechanical properties, the normal variation in measurement parameters to be utilized for power calculations has been estimated. These data were obtained through biomechanical tests of mouse patellar tendons in this laboratory following the same protocols as those to be used in the current proposal. To detect a moderate effect size of 1.2 at 80% power, 10 animals per group are needed (p<0.05). In recognition that multiple measures are observed for each tendon in each group, a Bonferroni correction for multiple comparisons are performed appropriately. Based on a similar calculation and given the expected variation in the angular deviation in measuring collagen organization (a measure of fiber distribution spread) from previous mouse patellar tendon experiments, four animals per group are needed.

Numbers of animals for other assays are sufficient to provide more qualitative information (no statistical evaluation to be performed). This information is expected to be supportive and to help explain the difference in the quantitative results. This information is also be useful for proposing potential mechanisms of alterations for future investigation.

Surgical Injury Model

The patellar tendon is injured in both legs of each mouse as detailed under the description of experiments section of this proposal.

For the surgical procedure, mice are administered buprenorphine as a pre-(0.1 mg/kg) and post-(0.5 mg/kg) operative analgesia. In preparation for the surgical procedure, mice are anesthetized with a mixture of isoflurane and oxygen, and both hindlimbs are shaved. The mice are placed in a supine position with the knee flexed. A skin incision medial to the knee is made and the skin pulled aside to expose the patellar tendon. Two cuts parallel to the tendon are made in the retinaculum on each side, and a plastic-coated blade is placed underneath the patellar tendon. With the coated blade serving as support, a 0.75 mm diameter biopsy punch (Shoney Scientific, Waukesha, Wis.) is used to create a full-thickness partial transection in the patellar tendon (see FIG. 3). The plastic backing is removed, leaving a distinct and reproducible injury.

Histological Evaluation

The histological and organizational testing follow previously established protocols developed in our laboratory. Four mice from the experimental groups are designated for histological and organizational analysis, and the patellar tendons is immediately dissected following sacrifice. The tendons are dissected free from the patella and tibia, processed with standard histological techniques and embedded in paraffin blocks. 7 μM cut parallel to the tendon fibers, and stained with H&E.

A qualitative analysis of the tissue slides is performed using light microscopy to assess the presence of foam cells and collagen fiber organization. This analysis is performed by assigning a rank to each of the observations where 0 indicates normal, 1 indicates mild changes, 2 indicates moderate changes, and 3 indicates marked changes. Standard images representing each grading level for each measure is prepared to provide consistency across graders. The histological analysis is performed independently and blindly by three graders on representative sections from each of these tendons. For each variable examined, measures from the three graders are averaged, yielding an overall histological grade for the tissue sections. This methodology has been used previously in our laboratory for histological tissue assessment.

The slides are also analyzed using a quantitative polarized light microscopy method developed in our lab. Grayscale images of the tendon are taken at 5° increments with crossed analyzer and polarizer simultaneously rotated through 90°. Subsequently, the filter is removed and images taken again at 5° C. increments while a X compensator is rotated through 90° along with crossed analyzer and polarizer. Custom-designed software is then utilized to determine collagen fiber orientations. This program allows the user to define the area of interest and the number of points within that area to be analyzed. Next, a graph of light intensity versus section orientation for each of the points is plotted. Extinction angles for each point are visually inspected, and points that do not follow a typical plot, as would be the case if the point were located on an empty space, are deleted. The average angle is then defined to be 90° C. for the purpose of statistical analysis.

Using a circular statistics package (Oriana version 1.06), collagen fiber distributions is statistically compared using a Chi-Squared method to test goodness of fit. To determine where the differences lie between samples, the angular deviation (AD) of the collagen orientations, a measure of fiber distribution spread, is also calculated.r is the length of the mean vector. This r value ranges from 0 to 1, with the larger numbers indicating that the observations are clustered more closely around the mean than lower numbers.

Immunohistochemical Evaluation

For the immunofluorescence analysis, the patellar tendons are immediately dissected following sacrifice. Similar to the organizational study, the tendons are also dissected free from the patella and tibia, processed, embedded in paraffin, and sectioned. The methods for immunohistochemical analysis include the following: tendons are embedded in paraffin. Serial sections (8 μm) of tissue are mounted on masked 10-well slides. Sections are fixed in acetone, air-dried and rehydratred in PBS containing 0.02% $NaN_3$, and blocked with 1% BSA in PBS/$NaN_3$. For detection of specific antigens, sections are reacted with the appropriate antibody followed by incubation with biotinylated anti-IgG antibody against the appropriate species, or reacted with biotinylated binding protein. Immunostaining is photographed on a Leica microscope using a Nikon 2020 or digitally captured.

The biomechanical testing follow previously established protocols. Ten mice from the experimental group are designated for geometric and biomechanical analysis. On the day of testing, specimens are thawed at room temperature before dissection. First, the entire left hindlimb is dissected free by severing the femur. This hindlimb is then be cleaned, leaving only the patella, patellar tendon, and tibia as one connected unit. The central area of interest in the patellar tendon is prepared as a standardized dumbbell-shaped specimen. A 0.1-mm thick double-edged razor blade is cut in half and each half bent within a custom device to create a consistent dumbbell-shaped stamp. Subsequently, two Verhoeff stain lines are placed on either end of the dumbbell shape on the tendon to serve as a gauge section for optical strain analysis. Next, the tendon width and thickness are quantified, and cross-sectional area calculated as the product of the two. Tendon width is measured using an optically based image processing system, and tendon thickness is quantified by lowering a fine indenter probe attached to a high-resolution linear variable differential transformer. After determining tendon width and thickness, the tibia is embedded in polymethylmethacrylate and secured in place with a metal pin. The potted specimen is then placed in PBS until testing, to be performed on the same day.

Figure 4:
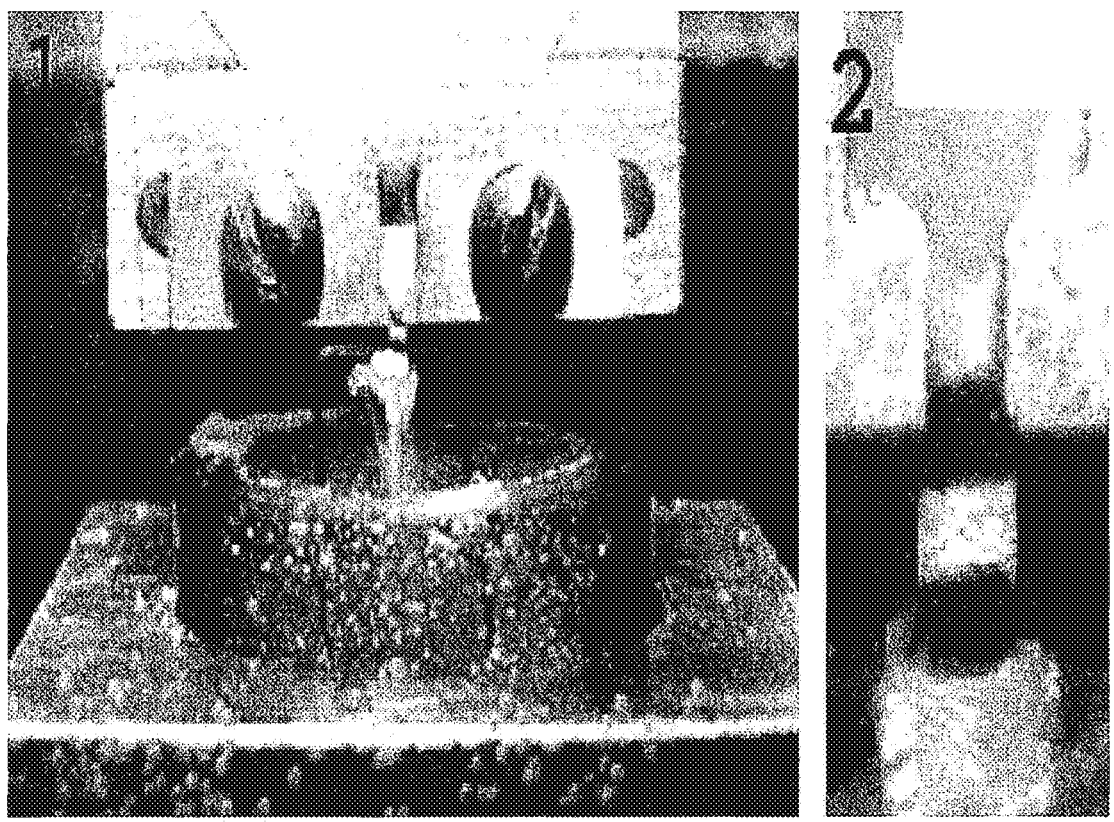
FIG. 4 is a photograph showing a patellar tendon placed in custom fixtures for mechanical testing.

The patella is held in place with a custom-designed cone-shaped wedge fixture, and the potted tibia end is secured to a custom-designed base (FIG. 4).

Each tendon specimen undergoes the following standard protocol: while immersed in a 37° C. saline bath—preloaded to 0.02 N at a rate of 0.1%/s (0.003 mm/s), preconditioned for 10 cycles from 0.02 to 0.04 N at a rate of 0.1%/s (0.003 mm/s), and held for 300 s. Immediately following this preconditioning, a stress-relaxation experiment is performed by elongating the tendon to a strain of 5% (0.15 mm) at a rate of 25%/s (0.75 mm/s), followed by a relaxation for 600 s. Finally, a ramp to failure is applied at a rate of 0.1%/s (0.003 mm/s). A custom written program in Labview is used to capture images during the test. Using the stain lines from these images, local tissue strain is measured optically.

Measures of elastic properties, stiffness and modulus are calculated using linear regression from the linear region of the load-displacement and stress-strain curves, respectively. Measures of viscoelastic properties, peak and equilibrium load and stress is determined from the stress relaxation curve. From these, the load ratio is calculated as the ratio of the equilibrium load to peak load values. As a method for further assessing the properties of the tendon, Fung's Quasi-linear Viscoelastic (QLV) Model is be 2) T1, and used to extract additional elastic (A and B) and viscous (C, parameters from the stress-relaxation experiment. These parameters are determined by curve-fitting data from the stress-relaxation portion of the protocol to the mathematical model as proposed by Fung with modifications to account for the finite ramp. Statistical analysis is performed using the student's t-test to compare between the control and experimental groups and =0.05.ausing the SYSTAT software package.

Example 1

The Effects of Hypercholesterolemia on Rotator Cuff Disease

Cholesterol data was collected on an age matched population of 240 patients: 120 of these patients (mean age 66.7) had ruptures of their rotator cuff tendons, while the control group consisted of 120 patients (mean age 65.4) seen in the orthopedic clinic for non-tendon related shoulder complaints. Total cholesterol (TC) and low-density lipoprotein cholesterol (LDL-C) concentrations of the patients with rotator cuff tendon tears were higher (p<0.05). 68% of the patients with rotator cuff tears had an elevated serum cholesterol, as compared to an overall rate of 24% in our control group. Using Hill's criteria for causality it was found that in patients with rotator cuff tears there was a positive correlation between mixed hyperlipidemia and rotator cuff tears.

This shows that the measurement of serum cholesterol in patients presenting with torn tendons provides with an opportunity to treat patients with hypercholesterolemia who otherwise may have gone undiagnosed and undertreated for years. This provides the opportunity to identify patients with hypercholesterolemia earlier and prevent the onset of such problems as future tendon ruptures, myocardial infarction, peripheral vascular disease, and cerebrovascular accidents. Future consideration of drug treatment specifically statin drugs may reduce the risk for future tendon degeneration, improve quality of life, decrease the risk of repair failure, and reduce morbidity and mortality.

Example 2

Injury Model

Figure 1:
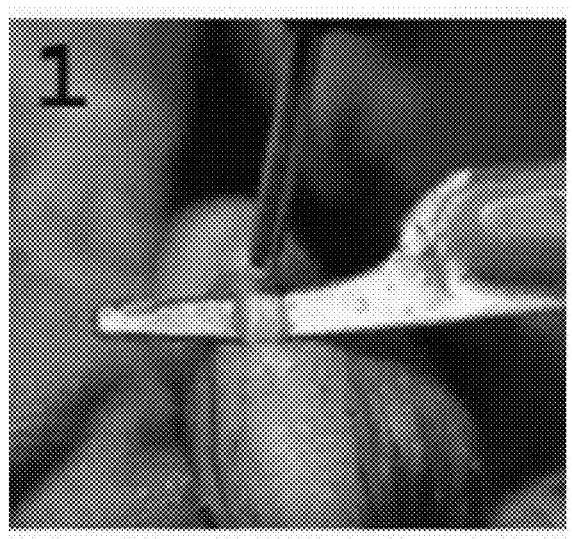
FIG. 1 is a photograph showing the circular punch that creates a partial transection in the middle half of the mouse patellar tendon.
Figure 2:
FIG. 2 is a photograph showing the defect on the patellar tendon after injury.

The patellar tendon model of the C57BL/6 mouse is a consistent and reproducible model of tendon injury with which this laboratory has extensive experience. The patellar tendon width in this particular mouse is 1.25 mm. The injury itself involved using a 0.75 mm diameter punch in the central portion of the tendon. With this partial-width transection, the marginal fibers in the periphery of the tendon would be left intact to allow for immediate post-operative tendon mobilization. These marginal fibers also circumvent the need for sutures, which can have harmful effects on the healing process and also eliminate the variability seen with surgical repair (FIGS. 1 and 2).

Figure 3:
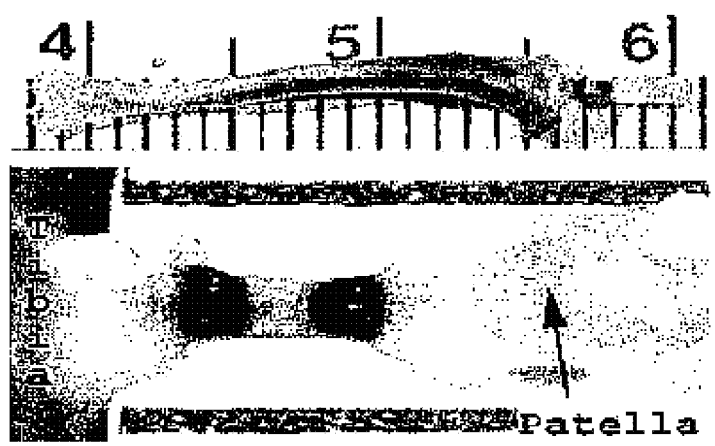
FIG. 3 shows a testing unit comprised of patella, patellar tendon, and tibia (top). Magnified picture of dumbbell-shape stamped patellar tendon with Verhoeff stain lines (bottom). Ruler in both pictures is in millimeters.

The superficial position of the mouse patellar tendon allows for easy identification and is also conducive to the delivery of agents to the patellar tendon that can modulate healing. Using the 0.75 mm diameter punch described above (60% of tendon width), a full thickness transection was created in the middle of the left patellar tendon with the right tendon undergoing a sham surgery. Details of this injury model are provided in the Methods and Materials section. For the organizational assay, tendons were processed with standard techniques (H&E stain) and viewed under polarized light (FIG. 3).

For biomechanical testing, each tendon specimen underwent preconditioning, a stress-relaxation experiment and a test to failure in a body temperature PBS bath.

Example 3

The Impact of Increased Serum Cholesterol

The increased serum cholesterol in the experimental group, leads to inferior collagen organization and thus worse biomechanical properties in the adult mouse tendon as compared to the control group. These significant findings prove the interaction of hypercholesterolemia and rotator cuff disease.

Example 4

Hypercholesterolemia is Detrimental to Tendon Properties and Healing in a Mouse Injury Model The objective of the present study was to evaluate tendon healing in normal and hypercholesterolemic mice at an advanced age using a patellar tendon injury model. The inventors of the instant application demonstrated that tendons from aging hypercholesterolemic mice exhibits inferior baseline mechanical properties and tendon healing compared to normal controls.

Twenty-four male C57BL/6 control mice (CTL) and 24 male C57BL/6 mice deficient for Apolipoprotein E (APOE) representing a hypercholesterolemia group were obtained (IACUC approved). These APOE mice have markedly elevated total plasma cholesterol levels as well as reduced high-density lipoprotein (HDL)-to-LDL ratios. For each group, ten animals were sacrificed without injury to provide baseline, uninjured data. Patellar tendons from the remaining 28 animals were injured. Briefly, incisions were made in the retinaculum adjacent to the tendon. A 0.75 mm diameter biopsy punch was used to create a full thickness, central (~60% width) defect in the left limb. The use of a central defect prevented the need for suture repair of the tendon. The right limb underwent a sham surgery, which included all procedures except for the defect itself. Skin incisions were closed and mice were allowed normal cage activity. Animals were sacrificed at 43 weeks of age (3 weeks post-injury for operated animals).

For biomechanical evaluation, patellar tendons (n=7-10 per group) were dissected, leaving the patella-tendon-tibia complex intact. Tendon cross-sectional area was measured using a custom laser-based device. The tendon was then stamped into a dumbbell shape and cross-sectional area was again measured for use in calculation of material properties.

The tibia was potted in PMMA and placed in custom fixtures. Specimens were submerged in a 37° C. PBS bath and tensile tested as follows: preload, preconditioning, stress relaxation for 10 minutes at 5% strain, return to gage length, and ramp to failure (0.1%/s). Tissue strain was measured optically.

Data were evaluated for differences in baseline and in healing between groups. For healing assessment, data from the injured limbs were normalized to that of the sham-operated contralateral limbs. Comparisons between CTL and APOE tendons were made using a one-tailed unpaired t-test for significance ($p \leq 0.05$) and trends ($0.05 < p \leq 0.1$).

Figure 5:
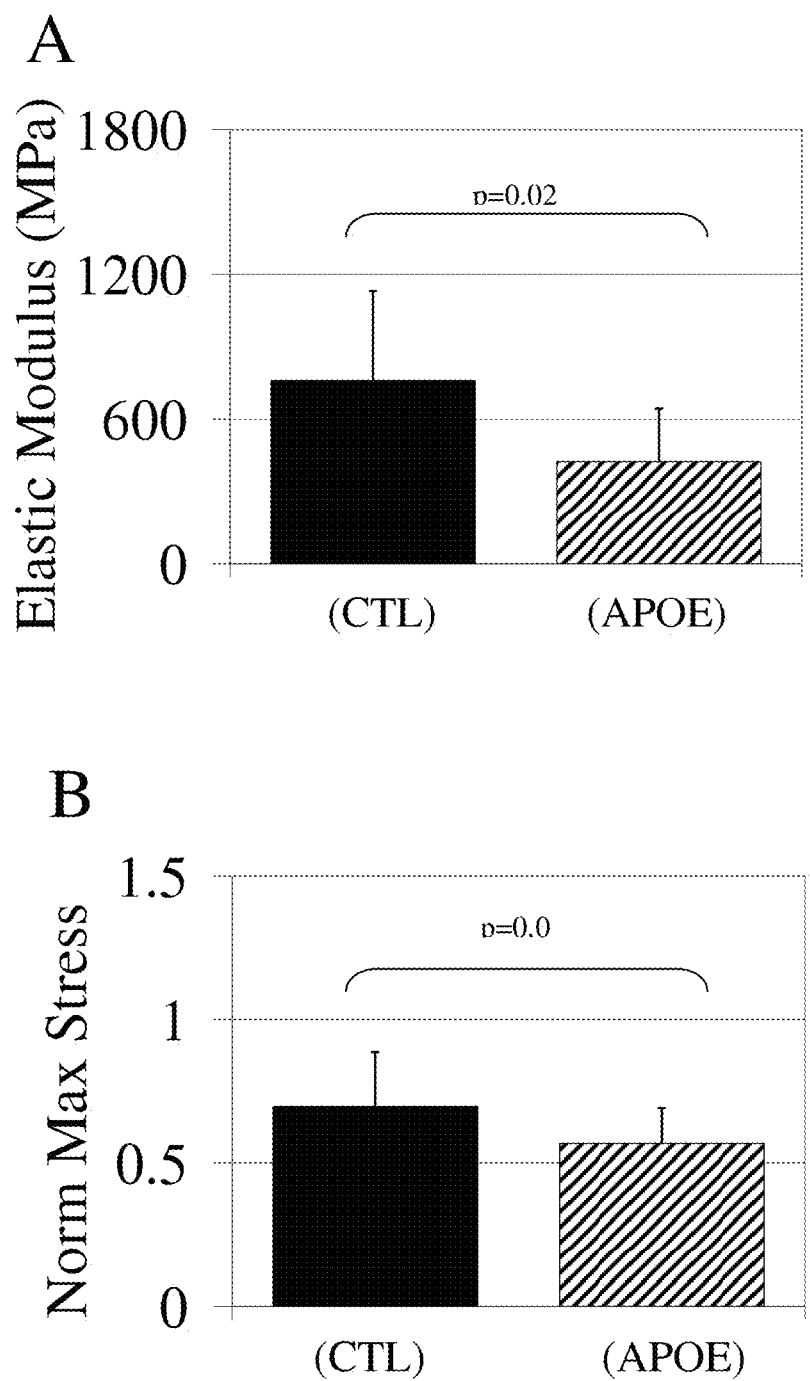
FIG. 5 shows (a) Elastic modulus of APOE uninjured tendons was significantly reduced compared to CTL; and (b)

Uninjured patellar tendons from APOE mice showed a significant decrease in elastic modulus (Table 1, FIG. 5A, $p=0.02$) and a trend toward increased cross-sectional area (Table 1, $p=0.1$) compared to control. For injured data, properties are presented as normalized ratios (injured/sham). Normalized maximum stress was significantly lower in the APOE group than in the controls (Table 1, FIG. 5B, $p=0.05$) and there were no differences in normalized area or modulus.

TABLE 1

Results from uninjured and normalized (injured/sham) paired tendons.

| | Uninjured Area ($mm^2$) | Uninjured Modulus (MPa) | Normalized Max Stress |
|---|---|---|---|
| CTL | 0.25 (0.05) | 759.6 (370.7) | 0.70 (0.19) |
| APOE | 0.28 (0.07) | 423.1 (220.1) | 0.57 (0.12) |
| p-value | 0.1[#] | 0.02* | 0.05* |

Data are presented are means (±SD).
p-values are denoted as *significant or [#]trends between CTL and APOE groups.

Healing was assessed in patellar tendons from normal (CTL) and hypercholesterolemic (APOE) mice. As hypothesized, APOE tendons exhibited reduced healing strength and baseline elastic modulus compared to controls.

The present results are contrary to the previous finding of improved healing strength in APOE tendons. As noted, the mice in the current study were appreciably older than in the previous study. The reduction in tendon healing in aging hypercholesterolemic tendons can be linked to the cumulative effects of intratendinous cholesterol deposition or relative tissue ischemia due to vascular compromise, as seen clinically in older patients. In summary, the inventors of the instant application have demonstrated reduced modulus and healing strength in hypercholesterolemic mice.

Example 5

High Cholesterol Adversely Affects Biceps Tendon Mechanical Properties in a Porcine Model The objective of this study was to investigate potential relationships between high cholesterol and shoulder tendon mechanics in an existing porcine model. The inventors of the instant application found that biceps tendons from hypercholesterolemic pigs have reduced mechanical properties when compared to those of normal controls.

A total of seven male Yorkshire pigs (103 kg average) were used in this IACUC-approved study. At 3-4 months of age, a control group (n=3) continued to receive a normal diet while a high cholesterol group (n=4) received a diet of 0.5% cholesterol, 10% lard, and 1.5% sodium cholate for a period of five months. At the end of the five month treatment, all animals were sacrificed. Biceps tendons were dissected from the right shoulder of each animal and prepared for biomechanical testing as described below.

Biceps tendons were dissected free from the muscle insertion, while leaving the bony insertion intact. The glenoid was then separated from the scapula using a pneumatic saw. To facilitate calculation of optical strain, three stain lines were placed on the tendon—one at the insertion above the glenoid and two others in the tendon midsubstance (FIG. 6), leaving a total gauge length of 30 mm Tendon cross-sectional area was measured using a custom laser-based device. The distal end of the biceps was fixed between two layers of sandpaper using a cyanoacrylate adhesive and clamped using custom serrated grips. The remaining portion of the scapula/glenoid was then potted in PMMA and placed in a base fixture (FIG. 6). Specimens were submerged in a 37° C. PBS bath and tensile tested as follows: preload, preconditioning, and ramp to failure at 0.1%/s. Data between groups were evaluated using a one-tailed unpaired t-test with significance set at $p \leq 0.05$.

Mean cholesterol levels at the time of sacrifice were 290 mg/dL for the hypercholesterolemic (HC) group and under 100 mg/dL for the control (CTL) group (no quantitative measure below 100 was recorded).

No differences were noted in tendon size as measured by cross-sectional area (Table 2). Biomechanical testing revealed significantly reduced stiffness ($p \leq 0.002$) and Young's modulus ($p \leq 0.0001$) in the HC group compared to CTL tendons (Table 2, FIG. 7). This finding was present for both tendon midsubstance and insertion site properties.

TABLE 2

Tensile testing data of pig biceps tendons.

| | Area ($mm^2$) | Insert. Stiffness (N/mm) | Midsub. Stiffness (N/mm) | Insert. Modulus (MPa) | Midsub. Modulus (MPa) |
|---|---|---|---|---|---|
| CTL | 25.9 (2.29) | 1289.0 (101.6) | 2976.9 (518.9) | 1024.3 (51.6) | 1194.2 (50.9) |
| HC | 24.2 (4.00) | 769.9 (82.9) | 1497.9 (261.7) | 656.5 (53.8) | 647.4 (76.2) |
| p-value | 0.3 | 0.0003* | 0.002* | 0.0001* | 0.00006* |

Data are presented as means (±SD).
*denotes statistical significance between control (CTL) and high cholesterol (HC) groups.

It was shown that tendons from hypercholesterolemic pigs would demonstrate inferior properties compared to normal control tendons. Mechanical testing demonstrated that biceps tendons of hypercholesterolemic animals were severely compromised compared to those of control animals. This is the first study reporting effects of hypercholesterolemia on native tendon mechanical properties. The present finding of substantially reduced mechanics supports our clinical observations relating high cholesterol and the incidence of tendon tears.

In this study, the inventors of the instant application have shown a detrimental effect of high cholesterol on normal tendon mechanics in the pig shoulder. While this study includes only a small sample size, the particularly low variance in the data and striking nature of the statistically significant results provide strong confidence in the findings.

Example 6

Effect of Diet-Induced Hypercholesterolemia on Rotator Cuff Tendon Mechanics in a Rat Model Materials and Methods Thirty male Sprague-Dawley rats (400-450 grams) were obtained with IACUC approval. Ten rats received a high-cholesterol diet consisting of 4% cholesterol and 1% sodium cholate (HC1 group). This experimental diet formulation has been shown to produce elevated total cholesterol values in Sprague-Dawley rats after three months. Another group of ten rats received a different diet formulation consisting of 2% cholesterol (HC2 group). This diet has resulted in increased total cholesterol, LDL, and triglycerides after two months, while also lowering beneficial high-density lipoprotein (HDL) levels. The remaining ten rats received standard chow and served as controls (CTL group). Both experimental diets (Research Diets, Inc., New Brunswick, N.J.) were formulated as a modification using the standard chow as a base. All rats were allowed food and water ad libitum for three months.

Following sacrifice, blood was collected and complete plasma lipid panels were assessed to measure total cholesterol (TC), high-density lipoprotein (HDL), and triglycerides (TG). In addition, the ratio of TC to HDL was calculated and evaluated as a clinically important value.

For biomechanical evaluation, the right supraspinatus tendon (n=10 per group) was dissected, leaving the humerus attached. Tendon cross-sectional area was measured using a custom laser-based device. The humerus was potted in PMMA and placed in custom fixtures. Specimens were submerged in a 37° C. PBS bath and tensile tested as follows: preload, preconditioning, stress relaxation for 10 minutes at 5% strain, return to gauge length, and ramp to failure at 0.3%/s. Tissue strain was measured optically using texture-correlation.

Comparisons were made separately between each high cholesterol group and the control group using t-tests.

Results

Lipid analysis (Table 3) confirmed that both high-cholesterol diets produced increased TC levels as well as TC:HDL ratios. Rats in the HC2 group also demonstrated a decline in HDL levels. Triglycerides were decreased in the HC1 rats. Biomechanical testing of supraspinatus tendons showed consistent increases in stiffness and elastic modulus in both high cholesterol rat groups (Table 4, FIG. 8) compared to control. Failure properties were not reported due to variances in failure mode.

TABLE 3

Lipid panel results for control and high-cholesterol diets. Data are presented as means ± standard deviations. p-values are presented for both cholesterol groups compared to control.

|  | TC (mg/dL) | HDL (mg/dL) | TG (mg/dL) | TC:HDL |
|---|---|---|---|---|
| CTL | 82 ± 20 | 40 ± 8 | 167 ± 41 | 2.1 ± 0.3 |
| HC1 | 355 ± 149 | 45 ± 13 | 121 ± 47 | 8.6 ± 4.6 |
| (p-value) | (0.00001) | (0.1) | (0.02) | (0.0001) |
| HC2 | 150 ± 33 | 20 ± 5 | 184 ± 63 | 5.9 ± 1.7 |
| (p-value) | (0.00001) | (0.0001) | (0.2) | (0.000001) |

TABLE 4

Biomechanical results from rat supraspinatus tendons. Data are presented as means ± standard deviations. P-values are presented for both cholesterol groups compared to control.

|  | Area (mm$^2$) | % Relax | Stiffness (N/mm) | Modulus (MPa) |
|---|---|---|---|---|
| CTL | 1.57 ± 0.34 | 64.4 ± 3.78 | 81.6 ± 24.3 | 229.9 ± 87.1 |
| HC1 | 1.52 ± 0.17 | 63.2 ± 4.87 | 101.8 ± 17.3 | 297.8 ± 72.3 |
| (p-value) | (0.3) | (0.3) | (0.02) | (0.04) |
| HC2 | 1.53 ± 0.18 | 65.1 ± 7.24 | 98.3 ± 23.2 | 286.1 ± 54.3 |
| (p-value) | (0.4) | (0.4) | (0.07) | (0.05) |

Native mechanical properties were assessed in supraspinatus tendons from normal rats and rats fed one of two high-cholesterol diets. Rats fed the high-cholesterol diets had elevated total cholesterol levels as well as increased total cholesterol to HDL ratios. The increased TC in the HC1 and HC2 groups, in addition to decreased HDL in the HC2 group, are consistent with findings in previous studies using these diets in Sprague-Dawley rats.

Surprisingly, tendons from both high-cholesterol rat groups had increased mechanical properties. Previous work in our lab has demonstrated reduced modulus in patellar tendons from genetically hypercholesterolemic mice as well as decreased stiffness and modulus in biceps tendons of pigs fed a high-cholesterol diet. The present findings of increased stiffness and modulus in hypercholesterolemic rats are in direct contrast to these previous results. This may be due to the differences in type, location, and function of the different tendons and how these relate to various intrinsic and extrinsic factors. While both three-month diet courses did produce marked increases in cholesterol as measured in the blood, this time frame may not have been long enough for the deleterious cumulative effects of hypercholesterolemia seen in our previous work and in other systems (e.g., cardiovascular) to reach the tendon level in this model given differences in cellularity and vascularity.

In summary, it was demonstrated that increased stiffness and modulus occurs in hypercholesterolemic rats.

Example 7

Hypercholesterolemia Increases Supraspinatus Tendon Stiffness and Elastic Modulus Across Multiple Species Materials and Methods Mouse:

Ten male C57BL/6 control (CTL) mice and ten C57BL/6 mice deficient for apolipoprotein E (APOE) representing a high-cholesterol (HC) group were used with Institutional Animal Care and Use Committee (IACUC) approval. These mice have markedly elevated plasma total cholesterol (TC) levels as well as increased TC-to-high-density lipoprotein cholesterol ratios (TC/HDL). All mice were allowed food and water ad libitum and sacrificed at 10 months of age.

Rat:

Twenty male Sprague-Dawley rats were obtained at 400-450 grams with IACUC approval. Ten rats received a high-cholesterol diet consisting of 4% cholesterol and 1% sodium cholate (HC) which has been shown by us and others to produce elevated TC values after three months. The other ten rats received standard chow and served as controls (CTL). All rats were allowed food and water ad libitum for 6 months and were then sacrificed. Blood was drawn immediately following sacrifice and plasma lipid profiles were obtained.

Monkey:

Supra spinatus tendons from ten male vervet (African green) monkeys were used as byproducts from a separate study with IACUC approval. The monkeys were fed diets containing 35% of energy as monounsaturated fat supplemented with cholesterol at 0.002 mg/kcal (CTL, n=5) and 0.4 mg/kcal (HC, n=5). At the end of the 2.5-month treatment, all monkeys were sacrificed and plasma lipid profiles were determined.

For all animals, supraspinatus tendons were dissected free from all muscle tissue, while leaving the bony insertion to the humerus intact. For mouse and rat specimens (animal masses on the order of 30 and 700 g, respectively), a stereomicroscope was used to ensure complete removal of peritendinous tissue. There were no noted differences in the amount of extraneous tissue removed from or remaining on tendons from normal and hypercholesterolemic animals. With an average animal mass of 6.7 kg, monkey fine dissections did not require magnification.

Local tissue strain was optically tracked using Verhoeff's stain lines placed on the tendon at three locations—one at the humeral insertion and two others in the tendon midsubstance (FIG. 9). A fourth stain line was used to mark the position of the grip and was used to assess slippage from the grips during testing.

Tendon cross-sectional area was calculated using a custom laser-based device, which measured tendon thickness at each stain line by scanning over the tendon using translational stages. Two orthogonal linear variable differential transformers (LVDTs) were used for position measurement and a charge-coupled device laser was used for thickness measurement. Using custom measurement and analysis software, an average cross-sectional area measurement was calculated for the tendon between the insertion site and the third stain line. Reported measurements of overall tendon stiffness and elastic modulus were also calculated between the stain lines at the insertion site and the upper-most stain line in the tendon midsubstance.

The tendon end was fixed between two layers of sandpaper using a cyanoacrylate adhesive and clamped with custom grips. The remaining portion of the humeral diaphysis was potted in poly(methyl) methacrylate with its longitudinal axis aligned with the pot and placed in a base fixture. For all species, the supraspinatus tendon was loaded in the direction on the long axis of the humerus rather than in its physiologic orientation of wrapping around the humeral head. This orientation was chosen based on previous work in our lab showing no differences in rat supraspinatus mechanical properties between these two orientations. In addition, this orientation would allow for comparisons with future data evaluating quantitative polarized light during mechanical testing, which requires light to be able to pass through the tendon.

Specimens were submerged in a 37° C. PBS bath and tensile tested to failure in an Instron 5543 mechanical test frame (Instron Corp., Norwood, Mass.) using a standard protocol. Briefly, tendons were preloaded to remove slack, followed by ten cycles of preconditioning between two species-scaled loads, and a 300 s hold. Next, a stress relaxation test was performed by ramping to 5% strain at 5%/s and relaxing for 600 s. Specimens were then returned to initial gauge length, held for 60 s, and finally ramped to failure at 0.1-0.3%/s. Data from mechanical testing (e.g., stiffness/modulus, maximum load/stress, percent relaxation) between CTL and HC for each species was evaluated using t-tests. Significance was set at p≤0.05 and trends were noted when p≤0.1.

Results

There were no noted differences in activity level between normal and hypercholesterolemic animals for any species. Plasma lipid analysis for mice, rats, and monkeys showed that all HC animals had significantly increased TC and TC/HDL cholesterol (Table 5). Overall, no differences were noted in animal mass between groups for any species. Similarly, no differences were noted in tendon size as assessed by cross-sectional area (Table 6).

TABLE 5

Results for supraspinatus tendons across species (means ± SD).

|       |     | Area (mm²)    | Stiffness (N/mm) | Modulus (MPa)      |
|-------|-----|---------------|------------------|--------------------|
| Mouse | CTL | 0.28 ± 0.04   | 95.1 ± 39.8      | 312.8 ± 127.0      |
|       | HC  | 0.26 ± 0.04   | 143.5 ± 43.6†    | 530.8 ± 196.3†     |
| Rat   | CTL | 1.56 ± 0.21   | 98.0 ± 20.4      | 325.7 ± 70.9       |
|       | HC  | 1.56 ± 0.19   | 123.3 ± 39.2†    | 416.9 ± 184.0‡     |
| Monkey| CTL | 10.26 ± 1.80  | 238.8 ± 72.9     | 328.2 ± 66.3       |
|       | HC  | 9.47 ± 1.10   | 312.4 ± 99.8‡    | 417.9 ± 48.0†      |

†denotes statistical significance compared to CTL;
‡denotes a trend.

TABLE 6

Geometrical and biomechanical results for supraspinatus tendons.

|        | Area (mm2)     | Peak load (N)   | Peak stress (MPa) | % Relaxation    | Stiffness (N/mm)  | Modulus (MPa)      |
|--------|----------------|-----------------|-------------------|-----------------|-------------------|--------------------|
| Mouse  |                |                 |                   |                 |                   |                    |
| CTL    | 0.28 +/- 0.04  | 0.93 +/- 0.34   | 3.40 +/- 1.56     | 34.9 +/- 9.57   | 95.1 +/- 39.8     | 312.8 +/- 127.0    |
| HC     | 0.26 +/- 0.04  | 0.83 +/- 0.27   | 3.06 +/- 1.05     | 36.2 +/- 6.79   | 43.5 +/- 43.6*    | 530.8 +/- 196.3*   |
| Rat    |                |                 |                   |                 |                   |                    |
| CTL    | 1.56 +/- 0.21  | 6.81 +/- 1.40   | 4.10 +/- 0.87     | 62.8 +/- 6.10   | 98.0 +/- 20.4     | 325.7 +/- 70.9     |
| HC     | 1.56 +/- 0.19  | 8.00 +/- 2.40†  | 4.99 +/- 1.88†    | 63.9 +/- 5.69   | 123.3 +/- 39.2*   | 416.9 +/- 184.0†   |
| Monkey |                |                 |                   |                 |                   |                    |
| CTL    | 10.26 +/- 1.80 | 60.7 +/- 15.83  | 6.01 +/- 1.53     | 34.6 +/- 5.58   | 238.8 +/- 72.9    | 328.2 +/- 66.3     |
| HC     | 9.47 +/- 1.10  | 64.7 +/- 8.93   | 6.06 +/- 0.83     | 35.3 +/- 4.67   | 312.4 +/- 99.8†   | 417.9 +/- 48.0*    |

Data are presented as mean +/- standard deviation. In general, stiffness and modulus were increased in HC animals across species.
*Statistically significant compared with CTL.
† Nonsignificant trend.

Biomechanical testing showed a significant increase in stiffness compared to CTL in HC mice and rats as well as a trend (p=0.1) in HC monkeys (Table 7). Elastic modulus (FIG. 10) was also increased in HC mice and monkeys, with HC rats exhibiting a trend (p=0.08). From the stress-relaxation test, peak load and peak stress showed a trend toward being increased in the HC rats, but not in other species. There were no differences in equilibrium load/stress or percent relaxation between groups for any species. Since failure occurred by tendon rupture at the grip interface for the majority of specimens, failure properties were not reported.

TABLE 7

Overall stiffness and elastic modulus changes due to high cholesterol.
▲ = significant increase; ↑ = trend.

|  | Mouse | Rat | Monkey |
|---|---|---|---|
| Stiffness | ▲ | ▲ | ↑ |
| Modulus | ▲ | ↑ | ▲ |

In this study, increased stiffness and modulus due to hypercholesterolemia in supraspinatus tendons has been demonstrated to occur in three different species of small and large animals. Previous work has demonstrated a variety of findings depending on species and tendon type, potentially due to differences in location and function (e.g., intrinsic/extrinsic, intra/extra-synovial, etc.). In particular, high plasma cholesterol was shown to reduce elastic modulus in mouse patellar tendons, decrease stiffness and modulus in pig biceps tendons, and increase stiffness and modulus in rat supraspinatus tendons. Aside from the difference in species, the discrepancy between the shoulder tendons (biceps and supraspinatus) results may be due to the different functions performed by the tendons. As one example, the biceps remains relatively static within the joint during shoulder abduction and rotation, sliding passively within the bicipital groove. By contrast, the supraspinatus is subjected to a greater degree of motion as a result of its insertion directly on the humerus and is subjected to a different intrinsic and extrinsic loading environment.

As mentioned previously, the present study has shown consistent results to our previous rat study, even after extending the rat diet time course from 3 to 6 months. Additionally, the present results show consistency not only across species, but also between small and large animal models. As an example, elastic modulus values varied less than 5% across species, demonstrating that the native tissue quality is similar. This consistency combined with the fact that the aged mice in our current work were exposed to lifelong hypercholesterolemia (as compared to the rats and monkeys which were subjected to high-cholesterol diets) lends support to the notion that these increased properties are inherent to the effect of hypercholesterolemia on the supraspinatus tendon rather than due to an effect of length of time exposed to the cumulative effects of high plasma cholesterol.

The current study found no differences in cross-sectional area comparing supraspinatus tendons from normal and hypercholesterolemic animals. This seems to be in contrast to clinical findings which report increased Achilles tendon thickness and cross-sectional area in patients with familial hypercholesterolemia as well as those which have correlated thickening of the Achilles tendon with carotid atherosclerosis in similar patient populations. There are no studies, however, demonstrating similar changes in geometry in the supraspinatus tendon.

Changes in stiffness and/or modulus may affect the overall performance of the tendon based on its particular function. In predominantly load-bearing applications, a higher stiffness would appear to be advantageous not only from an engineering perspective, but also to aid in the prevention of joint laxity. Conversely, an increased stiffness would also allow less stretching of the tendon prior to rupture at its ultimate load. In the case of the rotator cuff, increased stiffness of the individual tendons contributing to overall shoulder stiffness is generally considered to be detrimental to the range of motion and function of the joint overall; however, aiding in joint stability is a primary role of the rotator cuff tendons, which would tend to be improved with increased stiffness.

A large number of orthopedic patients are unaware of their lipid profile as these patients sometimes present to the orthopedist with joint complaints prior to ever having had a cholesterol screening by their primary care physician or internist. In fact, one study of patients presenting for Achilles tendon ruptures reported that, of the 83% who were hypercholesterolemic, only 23% were aware of this health condition. The correlation of hypercholesterolemia and Achilles tendon ruptures generally agrees with our previous clinical finding relating hypercholesterolemia to rotator cuff tears. Ultimately, the knowledge that alterations in tendon function are an indication of hypercholesterolemia could provide orthopedic clinicians with an opportunity to proactively obtain lipid screenings for at-risk patients at the onset of abnormal tendon function and prior to any cardiovascular manifestations.

Example 8

Rat Rotator Cuff Tendon-to-Bone Healing Properties are Adversely Affected by Hypercholesterolemia Materials and Methods Sixty-four male Sprague-Dawley rats (400-450 grams) were obtained with the approval of the Institutional Animal Care and Use Committee. Thirty-two rats received a high-cholesterol diet consisting of 4% cholesterol and 1% sodium cholate (HC group). This experimental diet (Research Diets, Inc., New Brunswick, N.J.) was formulated as a modification of the standard rat chow and has been shown by us and others to produce elevated total cholesterol values in Sprague-Dawley rats after three months. The other 32 rats received the standard chow and served as controls (CTL group). Over a period of six months, all rats were allowed food and water ad libitum and were weighed weekly. After the initial six-month treatment period, all animals were subjected to a standard, unilateral supraspinatus detachment and repair surgery. Briefly, the supraspinatus tendon was surgically exposed and sharply detached at the humeral insertion using a scalpel. Following detachment, the tendon was reattached to the greater tubercle of the humerus using a modified Mason-Allen technique.

Overlying musculature was sutured back and skin incisions were closed with staples. The contralateral limb remained uninjured and served as within-animal comparative data. Post-operatively, animals continued their respective diet courses and were allowed normal cage activity for two (n=4 per group), four (n=14), and eight weeks (n=14) at which points they were euthanized (FIG. 11) Immediately following sacrifice, blood was collected and later spun to obtain plasma. Plasma lipid panels were measured and assessed for TC, HDL, and TG. In addition, the ratio of TC to HDL (TC/HDL) was calculated as a clinically relevant parameter. Data were evaluated for differences in tendon healing between cholesterol groups. To assess healing, each injured-limb parameter was normalized to that of the uninjured contralateral limb such that a value of 1.0 would represent complete recovery and values of more or less than 1.0 indicate altered healing. Comparisons were made between CTL and HC groups using t-tests, with significance set at $p \leq 0.05$.

For biomechanical evaluation (n=10 per group), the supraspinatus tendon was fine dissected from the muscle, while preserving the humeral insertion. Verhoeff's stain was placed on the tendon at the insertion as well as two locations within the tendon midsubstance for optical measurement of local tissue strain using custom texture-correlation analysis software. Tendon cross-sectional area was measured near each stain line location using a custom device equipped with translational stages, two orthogonal linear variable differential transformers, and a charge-coupled device laser. The humeral diaphysis and head were potted in poly(methyl methacrylate) while keeping the insertion site undisturbed. The cylindrical potted end of the specimen was placed in a base fixture, while the tendon end was glued between two layers of sandpaper and clamped. Specimens were submerged in a 37° C. PBS bath and tensile tested using an Instron 5543 mechanical test frame (Instron Corp., Norwood, Mass.). Tendons were initially preloaded to 0.1 N, followed by ten cycles of preconditioning between 0.1 and 0.5 N at a strain rate of 0.4%/s. After a 300-second hold to achieve equilibrium, a 600-second stress relaxation experiment began with a ramp to 5% strain at 5%/s, followed by a return to gauge length and 60-second hold. Finally, specimens were quasistatically tested to failure at a rate of 0.3%/s. Key measurements included maximum (i.e., failure) load and stress, stiffness, elastic modulus, and percent relaxation (percent difference between peak and equilibrium stresses over the stress-relaxation).

For histological assays (n=4 per group), supraspinatus tendons were dissected, keeping the proximal humerus intact to preserve the tendon-to-bone insertion. The specimens were immediately fixed, decalcified, and processed using standard techniques. Following paraffin embedding, 7 μm coronal sections were collected, dried, and stained with hematoxylin and eosin. Photomicrographs were blindly graded by three observers for assessment of cellularity and cell shape based on a scale of 0 (normal), 1 (mild changes), 2 (moderate changes), and 3 (marked changes) as we have done previously. The same images were also analyzed for collagen organization using quantitative polarized light microscopy. Using this technique, angular deviation (a measure of disorganization) was calculated for each specimen.

Data were evaluated for differences in tendon healing between cholesterol groups. To assess healing in quantitative properties (i.e., biomechanical and organizational), each injured-limb parameter was normalized to that of the uninjured contralateral limb such that a value of 1.0 would represent full recovery and values of more or less than 1.0 would indicate altered healing. Comparisons were made between biomechanical and organizational data for CTL and HC groups using one-tailed t-tests. For histological grading, a single composite grade was derived from each set of three individual grades. To evaluate healing, a change scores technique was employed, which calculated the difference between the injured and uninjured contralateral limb grades for each animal. The resulting values were compared between CTL and HC groups using a nonparametric Mann-Whitney test, except in cases where there was no variation among grades within a group. In these cases, a Wilcoxon signed rank test was used in which the median of one group was compared to the value of the non-varying group. Significance for all statistical analyses was set at $p \leq 0.05$.

Over the course of the six-month diet period, two animals (one HC and one CTL) had to be euthanized for health reasons unrelated to the study design, reducing the sample size for two-week histology to n=3 per group. Lipid analysis (Table 8) demonstrated that the HC diet produced significantly increased TC, HDL, and TC/HDL at 4 and 8 weeks and increased TC and HDL at 2 weeks, but no significant differences in TG Animals in the HC group were significantly lighter than CTL at the first week of diet initiation as well as in the final three weeks for the animals in the 8-week post-surgical group (FIG. 12).

TABLE 8

Lipid panel results showing increased TC, HDL, and TC/HDL for HC groups at all time points. Data shown as means ± standard deviations.

| | | TC (mg/dL) | HDL (mg/dL) | TG (mg/dL) | TC/HDL |
|---|---|---|---|---|---|
| 2-wk | CTL | 106 ± 3 | 56.8 ± 6.3 | 153 ± 58 | 1.9 ± 0.2 |
| | HC | 688 ± 329 | 121.1 ± 16.0 | 253 ± 180 | 5.9 ± 3.4 |
| | (p-value) | (0.02) | (0.001) | (0.2) | (0.06) |
| 4-wk | CTL | 102 ± 22 | 52.3 ± 13.4 | 195 ± 97 | 2.0 ± 0.2 |
| | HC | 379 ± 115 | 97.9 ± 26.0 | 155 ± 55 | 4.1 ± 1.1 |
| | (p-value) | (0.00000002) | (0.000002) | (0.09) | (0.0000002) |
| 8-wk | CTL | 128 ± 36 | 54.2 ± 16.4 | 208 ± 76 | 2.3 ± 0.2 |
| | HC | 577 ± 390 | 90.8 ± 30.0 | 221 ± 200 | 6.5 ± 2.6 |
| | (p-value) | (0.0003) | (0.0002) | (0.4) | (0.000001) |

Normalized (injured/native) cross-sectional area was closer to normal (1.0) in the HC group for the 8-week animals Mechanical testing revealed a significant reduction in normalized stiffness compared to CTL at 4 weeks post-injury, but no difference at 8 weeks (Table 6, FIG. 11). Since failure occurred at the insertion site for the injured limb and primarily at the grip for the uninjured limb, true normalized failure properties were not able to be reported.

TABLE 9

Biomechanical and organizational properties from rat supraspinatus tendons normalized to contralateral uninjured limb data. Stiffness returned significantly closer to normal (1.0) for CTL rats at 4 weeks post-injury; however, area was closer to normal in HC rats at 8 weeks post-injury. Data as means ± standard deviations. P-values are for HC compared to CTL.

| | | Area | Percent Relaxation | Stiffness | Modulus | Angular Deviation |
|---|---|---|---|---|---|---|
| 4-wk | CTL | 5.11 ± 1.76 | 1.36 ± 0.29 | 0.28 ± 0.13 | 0.038 ± 0.008 | 0.71 ± 0.40 |
| | HC | 4.87 ± 1.52 | 1.44 ± 0.24 | 0.20 ± 0.06 | 0.040 ± 0.027 | 6.08 ± 7.02 |
| | (p-value) | (0.4) | (0.3) | (0.05) | (0.4) | (0.1) |
| 8-wk | CTL | 4.93 ± 0.88 | 1.65 ± 0.34 | 0.31 ± 0.09 | 0.040 ± 0.020 | 1.70 ± 1.14 |
| | HC | 3.64 ± 0.95 | 1.70 ± 0.37 | 0.33 ± 0.15 | 0.051 ± 0.037 | 2.65 ± 0.78 |
| | (p-value) | (0.004) | (0.4) | (0.4) | (0.2) | (0.1) |

Polarized light microscopy showed no difference in normalized angular deviation between CTL and HC rats at 2-weeks post injury and repair. Collagen organization trended toward being closer to normal at 4 and 8 weeks (Table 7); however, this finding was not significant (p=0.1). Results for cellularity and cell shape also showed no significant differences between CTL and HC rats.

TABLE 10

Cellularity and cell shape results from grading of histological samples. Data as medians ± interquartile range. P-values are for HC compared to CTL.

| | | Uninjured | | Injured | | Change Scores | |
|---|---|---|---|---|---|---|---|
| | | Cellularity | Cell Shape | Cellularity | Cell Shape | Cellularity | Cell Shape |
| 2-wk | CTL | 1.00 ± 0.50 | 2.00 ± 1.00 | 3.00 ± 0.00 | 2.00 ± 0.00 | 2.00 ± 1.00 | 0.00 ± 2.00 |
| | HC | 1.00 ± 0.00 | 1.00 ± 1.00 | 3.00 ± 0.00 | 2.00 ± 0.50 | 2.00 ± 0.00 | 1.00 ± 3.00 |
| | (p-value) | | | | | (1.0) | (0.7) |
| 4-wk | CTL | 1.00 ± 0.50 | 3.00 ± 0.50 | 3.00 ± 0.00 | 1.00 ± 0.25 | 2.00 ± 1.00 | −2.00 ± 1.00 |
| | HC | 0.00 ± 0.50 | 0.00 ± 1.50 | 3.00 ± 0.00 | 2.00 ± 0.50 | 3.00 ± 1.00 | 2.00 ± 5.00 |
| | (p-value) | | | | | (0.2) | (0.4) |
| 8-wk | CTL | 2.00 ± 0.50 | 2.00 ± 0.50 | 2.50 ± 1.00 | 1.00 ± 0.25 | 1.00 ± 2.00 | −1.00 ± 0.00 |
| | HC | 0.50 ± 1.00 | 1.50 ± 3.00 | 2.00 ± 0.50 | 2.00 ± 0.00 | 1.50 ± 1.00 | 0.50 ± 3.00 |
| | (p-value) | | | | | (0.6) | (0.3) |

Mechanical properties, collagen organization, and cell number/shape were assessed in healing supraspinatus tendons from normal (CTL) and high-cholesterol (HC) rats. As hypothesized, healing tendons from the HC group had reduced normalized stiffness at 4 weeks post-injury; however, this finding was not present in the 8-week group. Unexpectedly, the 8-week HC animals weighed significantly less than CTL in the 3 weeks prior to sacrifice. The difference in overall size of the animals at this time point may have contributed to the lack of 8-week stiffness differences. This diet course combined with this time point represents the farthest point to which our experiments have been carried out in this model. It is difficult to speculate as to whether or not the separation in masses would continue at a later time point or if the differences seen here were related to other more specific factors (e.g., animal husbandry).

Our current findings are generally in agreement with our previous clinical findings, which correlated hypercholesterolemia with rotator cuff injury. There are other clinical data, however, suggesting no relationship. This inconsistency in findings could potentially be due to differences in initial screening methodology (e.g., imaging, arthroscopy, etc.) used between the two clinical studies. The reduction in healing stiffness at 4 weeks is consistent with one of our previous studies in the mouse patellar tendon, which showed reduced elastic modulus due to lifelong exposure to high cholesterol.

In this study, injured tendon data was normalized to the contralateral limb to provide within-animal comparisons to preclude the need for analytical randomization techniques (e.g., bootstrapping) and thereby minimize data variation. Nevertheless, contralateral limb properties could have been affected by altered joint loading due to the injured limb and thus, may not represent normal properties. It should be noted, however, that purely native properties were not necessary to test our study hypothesis, which sought to assess the healing response of the tendon as opposed to establishing baseline magnitudes.

The high-cholesterol diet used in this study over the course of six months resulted in a marked increase (roughly 300%) in TC compared to normal and that levels of this magnitude would likely represent a profound cardiovascular pathology to a patient. It is worth noting that HDL (also known as good cholesterol) was also significantly increased, resulting in a TC/HDL increase on the order of roughly 150%. Also, the time scale during which the HC rats were on the altered diet (six months) could be considered much shorter in duration than that of a typical hypercholesterolemic patient, resulting in the relative exposures potentially being similar.

Often, patients presenting to orthopedic surgeons have little to no knowledge regarding their serum lipid profiles. One study has reported that orthopedic patients with often unknown familial hypercholesterolemia typically present with Achilles tendon pain more than twenty years prior to being referred to a lipid clinic. Further, another study of patients presenting for Achilles tendon ruptures reported that 83% of those patients were hypercholesterolemic and more than three-quarters of those were unaware of this fact. The overall body of work in this area could be beneficial to patients with previously undiagnosed hypercholesterolemia by providing their physicians with a tool for detection of this serious health condition before the appearance of the associated adverse cardiovascular symptoms. Conversely, knowledge that elevated serum cholesterol could increase the risk for tendon injury or reduce the healing ability of existing injuries could also be valuable to patients with existing tendon injuries or non-injured high-risk patients who perform repetitive tasks, eccentric loading activities, or motions outside the normal range.

In summary, decreased healing stiffness in hypercholesterolemic rats at 4 weeks following supraspinatus injury and repair has been demonstrated. Based on these findings, hypercholesterolemia has a detrimental effect on tendon healing in our rat rotator cuff injury and repair model.

Example 9

Atorvastatin for Treating a Patellar Tendon Injury

A 40 year old male presents with a partial tear of the patellar tendon. His orthopedist orders a standard lipid panel as part of his blood work. The orthopedist finds that the patient is hypercholesterolemic with a total cholesterol of almost 300 mg/DL. The orthopedist prescribes atorvastatin to be taken orally at a dose of 20 mg once daily. In addition to lowering his cholesterol to acceptable levels, the patient's recovery from his partial tear of the patellar tendon is markedly improved by the statin administration.

Example 10

Simvastatin for Treating Tennis Elbow

A 50 year old obese female smoker presents with lateral epicondylitis (tennis elbow). Her primary care physician orders a standard lipid panel as part of her blood work. The physician finds that the patient is hypercholesterolemic with a total cholesterol of almost 260 mg/DL. The physician prescribes simvastatin to be taken orally at a dose of 10 mg once daily in the evening. In addition to lowering her cholesterol to acceptable levels, the patient's recovery from her tennis elbow is markedly improved by the statin administration.

Example 11

Rosuvastatin for Treating an Achilles Tendon Injury

A 45 year old male diabetic presents with a partial rupture of his achilles tendon. His orthopedist orders a standard lipid panel as part of his blood work. The orthopedist finds that the patient is hypercholesterolemic with a total cholesterol of 285 mg/DL. The orthopedist prescribes rosuvastatin to be taken orally at a dose of 10 mg once daily. In addition to lowering his cholesterol to acceptable levels, the patient's recovery from his partial rupture of his achilles tendon is markedly improved by the statin administration.

Example 12

Pravastatin for Treating a Rotator Cuff Tear

A 35 year old female presents with a rotator cuff tear following a shoulder injury occurring during a basketball. Her orthopedist orders a standard lipid panel as part of her blood work. The orthopedist finds that the patient is hypercholesterolemic with a total cholesterol of 275 mg/DL. The orthopedist prescribes pravastatin to be taken orally at a dose of 40 mg once daily. In addition to lowering her cholesterol to acceptable levels, the patient's recovery from her rotator cuff tear is markedly improved by the statin administration.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating a tendinous or musculoskeletal soft tissue injury, in a subject with hypercholesterolemia, comprising systemically administering to said subject with hypercholesterolemia a therapeutically effective amount of a cholesterol lowering agent, wherein said soft tissue injury is a tendon injury, and wherein the cholesterol lowering agent is a statin.

2. The method of claim 1, wherein said tendinous injury is a rotator cuff injury, a knee tendon injury, a wrist tendon injury, an elbow tendon injury, a lateral epicondylitis, a medial epicondylitis, a flexor tendon injury, an extensor tendon injury, an achilles tendon injury, a patellar tendon injury, a peroneal tendon injury, a biceps tendon injury, or an overuse tendon injury.

3. The method of claim 1, wherein the statin is atorvastatin, cerivastatin, fluvastatin, lovastatin, mevastatin, pitavastatin, pravastatin, rosuvastatin, simvastatin, or a combination thereof.

4. The method of claim 1, wherein said subject with hypercholesterolemia has concentrations of TC higher than 240 mg/DL, HDL-C lower than 40 mg/DL, LDL-C higher than 130 mg/DL, or TG higher than 150 mg/DL in a serum sample from said subject.

5. The method of claim 4, wherein said subject with hypercholesterolemia has concentrations of TC higher than 240 mg/DL, HDL-C lower than 40 mg/DL, LDL-C higher than 130 mg/DL, and TG higher than 150 mg/DL in a serum sample from said subject.

6. The method of claim 5, wherein said statin lowers said subject's blood total cholesterol concentration below about 240 mg/dL.

7. The method of claim 5, wherein said statin lowers said subject's blood LDL-C to below about 130 mg/DL.

8. The method of claim 5, wherein said statin raises said subject's blood HDL-C to above about 40 mg/DL.

9. The method of claim 5, wherein said statin lowers said subject's blood TG to below about 150 mg/DL.

10. The method of claim 1, further comprising treating inflammation associated with said tendon injury.

11. The method of claim 1, further comprising treating edema associated with said tendon injury.

12. The method of claim 1, wherein treating said tendon injury comprises ameliorating symptoms associated with said tendon injury in said subject.

13. The method of claim 1, wherein treating said tendon injury comprises accelerating the healing of said tendon injury in said subject.

14. A method of reducing the risk of recurrence of a tendon injury, in a subject with hypercholesterolemia who previously had said tendon injury, comprising systemically administering to said subject with hypercholesterolemia a therapeutically effective amount of a cholesterol lowering agent, and wherein the cholesterol lowering agent is a statin.

15. The method of claim 14, wherein said tendon is a rotator cuff, a knee tendon, a wrist tendon, an elbow tendon, a flexor tendon, an extensor tendon, an achilles tendon, a patellar tendon, or a peroneal tendon.

16. The method of claim 14, wherein the statin is atorvastatin, cerivastatin, fluvastatin, lovastatin, mevastatin, pitavastatin, pravastatin, rosuvastatin, simvastatin, or a combination thereof.

17. The method of claim 14, wherein said subject with hypercholesterolemia has concentrations of TC higher than 240 mg/DL, HDL-C lower than 40 mg/DL, LDL-C higher than 130 mg/DL, or TG higher than 150 mg/DL in a serum sample from said subject.

18. The method of claim 14, wherein said subject with hypercholesterolemia has concentrations of TC higher than 240 mg/DL, HDL-C lower than 40 mg/DL, LDL-C higher than 130 mg/DL, and TG higher than 150 mg/DL in a serum sample from said subject.

19. The method of claim 18, wherein said statin lowers said subject's blood total cholesterol concentration below about 240 mg/dL.

20. The method of claim 18, wherein said statin lowers said subject's blood LDL-C to below about 130 mg/DL.

21. The method of claim 18, wherein said statin raises said subject's blood HDL-C to above about 40 mg/DL.

22. The method of claim 18, wherein said statin lowers said subject's blood TG to below about 150 mg/DL.

23. The method of claim 18, further comprises obtaining a serum sample from said subject; determining the concentration of TC, HDL-C, LDL-C, TG or their combination in said sample; and comparing the concentration in said sample to a standard that comprises the concentrations of TC at 240 mg/DL, HDL-C at 40 mg/DL, LDL-C at 130 mg/DL, and TG at 150 mg/DL.

* * * * *